US012755820B2

(12) United States Patent
Schenck et al.

(10) Patent No.: US 12,755,820 B2
(45) Date of Patent: Oct. 6, 2026

(54) SYSTEMS AND METHODS FOR PREDICTING HEMATOLOGICAL CONDITIONS USING METHYLATION DATA

(71) Applicant: H. LEE MOFFITT CANCER CENTER AND RESEARCH INSTITUTE, INC., Tampa, FL (US)

(72) Inventors: Ryan Schenck, Tampa, FL (US); Alexander Anderson, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 18/845,947

(22) PCT Filed: Mar. 13, 2023

(86) PCT No.: PCT/US2023/015101
§ 371 (c)(1),
(2) Date: Sep. 11, 2024

(87) PCT Pub. No.: WO2023/172772
PCT Pub. Date: Sep. 14, 2023

(65) Prior Publication Data

US 2025/0182864 A1 Jun. 5, 2025

Related U.S. Application Data

(60) Provisional application No. 63/319,031, filed on Mar. 11, 2022.

(51) Int. Cl.
*G16H 50/20* (2018.01)
*C12Q 1/6883* (2018.01)
(Continued)

(52) U.S. Cl.
CPC ........... *G16H 10/40* (2018.01); *C12Q 1/6883* (2013.01); *G16B 20/10* (2019.02); *G16B 20/20* (2019.02);
(Continued)

(58) Field of Classification Search
None
See application file for complete search history.

(56) References Cited

U.S. PATENT DOCUMENTS

2019/0316209 A1* 10/2019 Hubbell ............... C12Q 1/6806
2021/0010076 A1 1/2021 Delubac et al.

FOREIGN PATENT DOCUMENTS

WO WO-2013177265 A1 * 11/2013 ........... C12Q 1/6886

OTHER PUBLICATIONS

Gabbutt et al.: "Fluctuation methylation clocks for cell lineage tracing at high temporal resolution in human tissues"; May 2020 (Year: 2020).*

(Continued)

*Primary Examiner* — John A Pauls
(74) *Attorney, Agent, or Firm* — Meunier Carlin & Curfman LLC

(57) ABSTRACT

Systems and methods for predicting hematological conditions using methylation data are described herein. An example computer-implemented method includes: receiving patient data associated with a blood specimen from a subject, the patient data including fluctuating methylation clock (FMC) data; inputting the FMC data into a trained machine learning model; and predicting, using the trained machine learning model, a hematological condition in the subject.

19 Claims, 21 Drawing Sheets

(51) Int. Cl.
*G16B 20/10* (2019.01)
*G16B 20/20* (2019.01)
*G16H 10/40* (2018.01)

(52) U.S. Cl.
CPC ....... *G16H 50/20* (2018.01); *C12Q 2600/154* (2013.01)

(56) References Cited

OTHER PUBLICATIONS

Blecua at al.: "The DNA methylation landscape of hematological malignancies: an update"; Molecular Oncology 14; Jul. 3, 2020 (Year: 2020).*

International Search Report and Written Opinion mailed Jun. 14, 2023, from International Application No. PCT/US2023/015101, 9 pages.

Gabbutt et al., "Fluctuating methylation clocks for cell lineage tracing at high temporal resolution in human tissues," Nature Biotechnology, Jan. 3, 2022 (Jan. 3, 2022), vol. 40, No. 5, 17 pages.

* cited by examiner

| Algorithm | Marker | AUC | Accuracy | $F_1$ | Precision | Recall |
|---|---|---|---|---|---|---|
| Gaussian Naive Bayes | | 0.88 | 88.3% | 0.863 | 1.00 | 0.759 |
| Calibrated Gaussian Naive Bayes | | 0.903 | 90.5% | 0.895 | 0.971 | 0.83 |

SYSTEMS AND METHODS FOR PREDICTING HEMATOLOGICAL CONDITIONS USING METHYLATION DATA

CROSS-REFERENCE TO RELATED APPLICATIONS

This application is a United States National Phase Patent Application of International Patent Application Number PCT/US2023/015101, filed on Mar. 13, 2023, which claims the benefit of U.S. provisional patent application No. 63/319,031, filed on Mar. 11, 2022, and titled "METHODS FOR USING METHYLATION DATA TO PREDICT WHETHER A PATIENT HAS CHIP (CLONAL HEMATOPOIESIS OF INDETERMINATE POTENTIAL)," the disclosures of which are expressly incorporated herein by reference in their entirety.

STATEMENT REGARDING FEDERALLY FUNDED RESEARCH

This invention was made with government support under Grant no. CA143970 awarded by the National Institutes of Health. The government has certain rights in the invention.

BACKGROUND

Clonal hematopoiesis (CH), characterized as the homogenization of the hematopoietic stem cell population, can range from benign age-related CH (ARCH) to CH driven by specific oncogenic driver point mutations (e.g., CHIP). CH carries a significantly increased risk of cardiovascular events (e.g., myocardial infarctions), epithelial malignancies, and development of a hematological malignancy (11-13 times higher). The genetic complexity—known mutation type, mutation burden, and their frequencies—is an important distinguishing feature between CH and more aggressive disease. However, at this point in time, several drivers of mono/oligoclonal development are unknown and molecular diagnostics fails to screen for structural variants (copy number and translocations) that can be insightful for prognosis.

At present the gold standard for diagnosing hematological diseases without abnormal cytomorphologies is through Deoxyribonucleic acid (DNA) sequencing or single nucleotide polymorphism (SNP) arrays of specific point mutations whose variant frequencies are ≥2%. Studies have shown this diagnostic approach is insufficient at detecting CH in patients with either unknown oncogenic drivers or those with structural genomic variants (copy number changes or translocations), some of which are the strongest prognostic indicators to progression from CH to myeloid leukemias. Further, this method is unable to determine the aggressiveness of CH clones and life histories of CH in patients, preventing insights for clinical decision making beyond the presence/absence of CH or myolodysplastic syndrome (MDS).

Thus, there is a need in the art for a diagnostic approaches that are far more powerful, cheaper, and provides earlier insights into hematological diseases.

SUMMARY

In some implementations, the techniques described herein relate to a computer-implemented method including: receiving patient data associated with a blood specimen from a subject, the patient data including fluctuating methylation clock (FMC) data; inputting the FMC data into a trained machine learning model; and predicting, using the trained machine learning model, a hematological condition in the subject.

In some implementations, the FMC data includes DNA methylation fluctuation data for a plurality of fluctuating CpG (fCpG) sites.

In some implementations, the patient data further includes one or more DNA alteration markers. For example, the one or more DNA alteration markers can include a single nucleotide variant (SNV), a copy number alteration (CNA), or a structural variant (SV).

In some implementations, the step of predicting, using the trained machine learning model, the hematological condition includes diagnosing the subject with the hematological condition.

In some implementations, the step of predicting, using the trained machine learning model, the hematological condition includes providing a prognosis of the hematological condition.

In some implementations, the hematological condition is clonal hematopoiesis (CH). In some implementations, the hematological condition is clonal hematopoiesis of indeterminate potential (CHIP). In some implementations, the hematological condition is age related clonal hematopoiesis (ARCH).

In some implementations, the trained machine learning model is a random forest classifier.

In some implementations, the techniques described herein relate to a method including: receiving a blood specimen from a subject; obtaining, using a microarray, fluctuating methylation clock (FMC) data associated with the blood specimen; and inputting, using a computing device, the FMC data into a trained machine learning model; and predicting, using the trained machine learning model, a hematological condition in the subject.

In some implementations, the method further includes recommending, using the computing device, a course of treatment for the subject based on the predicted hematological condition.

In some implementations, the method further includes recommending performing a course of treatment on the subject based on the predicted hematological condition.

In some implementations, the techniques described herein relate to a system including: at least one processor and a memory operably coupled to the at least one processor, the memory having computer-executable instructions stored thereon that, when executed by the at least one processor, cause the processor to: receive patient data associated with a blood specimen from a subject, the patient data including fluctuating methylation clock (FMC) data; input the FMC data into a trained machine learning model; and predict, using the trained machine learning model, a hematological condition in the subject.

In some implementations, the FMC data includes DNA methylation fluctuation data for a plurality of fluctuating CpG (fCpG) sites.

In some implementations, the patient data further includes one or more DNA alteration markers. For example, the one or more DNA alteration markers can include a single nucleotide variant (SNV), a copy number alteration (CNA), or a structural variant (SV).

In some implementations, the step of receiving, using the trained machine learning model, the predicted hematological condition includes receiving a diagnosis or prognosis of the hematological condition.

In some implementations, the predicted hematological condition is clonal hematopoiesis (CH), clonal hematopoiesis of indeterminate potential (CHIP), or age related clonal hematopoiesis (ARCH)

In some implementations, the trained machine learning model is a random forest classifier.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 5A: The variance of the fCpG methylation distribution is a proxy for the rapidity of the clonal expansion within the blood. In normal samples the large stem cell population size leads to the methylation distribution being concentrated near 50% (as one would expect for uncorrelated oscillators). However, as a clonal cancerous population expands, clonal peaks begin to separate from the 50% peak. In the case of Acute lymphoblastic leukemias (ALL), the large, well-separated peaks near 0% and 100% are indicative of a single clonal population making up the majority of the remaining stem cells following rapid growth. FIG. 5B: Simulations confirm that a simple HSC model can recapitulate the observed methylation distribution overserved in patient data. Data presented as standard error of the mean (SEM). FIG. 5C: The variance of the fCpG methylation distribution experiences a gradual increase with age in normal patients. Confidence band was calculated via bootstrapping and represents 95% confidence intervals. FIG. 5D: The variance of paired blood samples taken 10 years apart (1997 and 2007) also exhibits a small but marked increase (0.37 Cohen's d, $p=2.8*10^{-5}$ two-sided paired t-test). FIG. 5E: Significant differences are observed in acute myeloid leukemias (AML) patients that are predominantly older than 50 years old compared to pediatric patients younger than 18 years old. Comparisons of fCpG β distribution variance shows that pediatric samples with ages less than 18 (GSE133986) exhibit higher variance than an older patient cohort (19 patients in this cohort are <50 years old; GSE62298) (two-sided Welch's t-test, $P=7.1*10^{-8}$). Confirmed normals are those presented within this study. FIG. 5F: Stratification of the pediatric cohort fails to reveal any significant differences in fCpG β distribution variances (two-sided Welch's t-test, P=0.08). For FIGS. 5A, D, E, and F center line, median; box limits, upper and lower quartiles; whiskers, 1.5/QR.

FIG. 6A: Cohort characteristics for CH samples presented here, including driver mutation variant allele frequency (VAF) and burden, sex, age, and cohort group. FIG. 6B: There is no difference between patients containing DNMT3A and TET2 mutations in both their VAF or age (center line, median; box limits, upper and lower quartiles; whiskers, 1.5 IQR; two-sided Welch's t-test, P>0.05). Overall, there is no increase in mutation's VAF across the age of the patients. The bottom row shows minimal increase in fCpG variance correlated with age and a slight correlation with driver VAF. No significant differences in fCpG variance is observed between DNMT3A, TET2, and other drivers. FIG. 6C: Variances of fCpG methylation distributions now including the confirmed normal controls ('Oxford Normal') and CH samples. For FIGS. 6B and 6C plots show center line, median; box limits, upper and lower quartiles; whiskers, 1.5 IQR. All ribbons show the calculated 95% confidence interval for the regression.

FIG. 7A: Illustration of an exemplary fCpG β distribution for a normal and CH sample where bootstrapping provides a larger number of samples for machine model train/test datasets used for the FMC-CH classifier (center line, median; box limits, upper and lower quartiles; whiskers, 1.5/QR). FIG. 7B: Random forest machine learning model provides the greatest performance where data pre-processing balances the precision and recall. FIG. 7C: The FMC-CH classifier is most useful for clones greater than 2%. Error bars (bottom) denote 95% confidence intervals for the CH prediction probability from 200 classifications. FIG. 7D: Simulations with varying expansion rates, E, determine time when the classifier will diagnose CH; however, prediction probabilities increase as the subclonal population expands (plots show mean of 25 simulations with mean and ribbons showing SEM). FIG. 7E, left: Comparison of the earliest time when diagnosis would be made using the gold standard VAF with the FMC-CH classifier shows faster expanding clones are detected earlier, while slower clones are detected later. This relationship is quantified to show that the relative detection time decreases exponentially as expansion rates increase (FIG. 7E, right) (Data shown is from 26 replicates for each parameter combination shown in FIG. 7D).

FIG. 8A (left): Retrospective classification using the FMC-CH classifier on two large publicly available normal cohorts' peripheral blood fCpG methylation sites (GSE40279 (n=656) and GSE87571 (n=732)). Across the cohorts the CH classifier finds evidence of 29.1% to 19.8% in each cohort respectively. FIG. 8A (right): A significant difference in age for the individuals in each cohort is apparent, where those classified as having CH are significantly older (GSE40279: −0.77 Cohen's d, $P=3.13*10^{-18}$; GSE87571: −0.54 Cohen's d, $P=7.90*10^{-09}$, both P-values from two-sided Welch's t-tests). FIG. 8B: fCpG beta distribution variances from the classified CH are not significantly different from those used to train and evaluate the FMC-CH classifier. Combined (to the right of the black, dashed line), we see the expected increase in fCpG beta distribution variances for samples exhibiting CH. FIG. 8C: CNA analysis on newly classified CH and normal samples reveals a significant increased overall CNA burden, a slightly significant increase in CNA gains (CNgains), and a more significant increase in CNA losses (CNloss) for the classified CH samples (CNA burdens $P=8.26*10^{-5}$; CNgains P=0.022; CNloss P=0.00025). FIG. 8D: The frequency of individuals with a presence of CNAs in the classified CH samples across both cohorts increases with age from 0.27% for those younger than 50 to 11.14% for those >70 years old (P=0.0013, chi-squared test). FIG. 8E: CNA calls using the samples not classified as CH as the reference we see several recurrent genomic positions across the autosomes where losses and gains are observed. Shown is the frequency of gains/losses in the shown genomic regions for each cohort's CH samples. Several of these losses/gains involve regions where oncogenic/CH driver genes are present (black dots). All boxplots show center line, median; box limits, upper and lower quartiles; whiskers, 1.5IQR.

FIG. 9A: Baseline simulation of a single clone with three different expansion rates (0.0625, 0.125, and 0.25) in an initial population of 500 HSCs revealing the delayed detection time for slower expanding clones. Lines are mean of 20 replicates with ribbons representing the standard error of the mean (SEM). Arrows of the same color denote the mean detection time based on classification using the FMC-CH classifier. FIG. 9B: Mean detection time for the single subclone simulations in FIG. 9A along with the SEM. FIG. 9C: The time to reach the mean steady state fCpG variance increases with slower expanding clones, by spreading out induction times this time is increased further (maximum allowed is 100 years). FIG. 9D: Presence of multiple subclones allows for earlier or the same detection time as a single clone, regardless of how far apart the clones are when they emerge. Points show the mean while error bars denote standard error of the mean (SEM).

FIG. 10A and FIG. 10B show mutation results from the PB samples in the CH patient cohort. FIG. 10A: CH patient samples with multiple drivers' trend towards a higher fCpG variance (Cohen's d=−0.58; two-sided Welch's t-test, P=0.089; center line, median; box limits, upper and lower quartiles; whiskers, 1.5 IQR). FIG. 10B, left: Shows the shift in frequency from the driver subclone with the maximum VAF (e.g., clone used for diagnosis) to the sum of all driver mutation subclonal VAF. The arrow connects these adjusted frequencies. FIG. 10B, right: Cumulative frequencies have a stronger correlation compared to the subclonal driver used for diagnosis (FIGS. 6A-6C). FIG. 10C through FIG. 10F show mutation results from paired BM patient samples in the CH patient cohort. FIG. 10C: There is a strong correlation between the frequencies of the same mutation in the PB and the BM (red dashed line shows the location for equal frequencies; linear regression shows $VAF_{BM} \approx VAF_{PB}*0.73+0.01$; r-squared=0.86; $P=3.5*10^{-30}$). FIG. 10D: The dominant driver differs in a small number of CH paired PB/BM samples. FIG. 10E: Frequency shifts between the largest subclonal driver and the cumulative sum of subclonal drivers just as in the PB (FIG. 10B). FIG. 10F: Just as in the PB results we see a stronger correlation of fCpG variance with the cumulative sum of driver subclones (bottom) compared to only the largest subclonal driver mutation (top). All ribbons show the calculated 95% confidence interval for the linear regression.

FIG. 11A: Subclonal compositions confirmed for four patient samples from single cell sequencing for two patients with nested subclonal drivers (NOC062 and NOC137) and two patients with concurrent drivers (NOC115 and NOC131). FIG. 11B: Corrected frequencies with confirmed subclonal structures, where the largest driver VAF for nested drivers and the cumulative sum of frequencies for concurrent drivers show correlation with fCpG variance for both BM and PB (stars in A indicate frequencies for each sample used). FIGS. 11C-11E illustrate qualitatively that these frequencies are approximately similar to those observed for patient NOC137 whose frequency of the primary driver VAF is 0.16 for ASXL1 and its nested driver VAF, TET2, is 0.041 with a corresponding fCpG variance just under 1.5.

DETAILED DESCRIPTION

Figure 1:
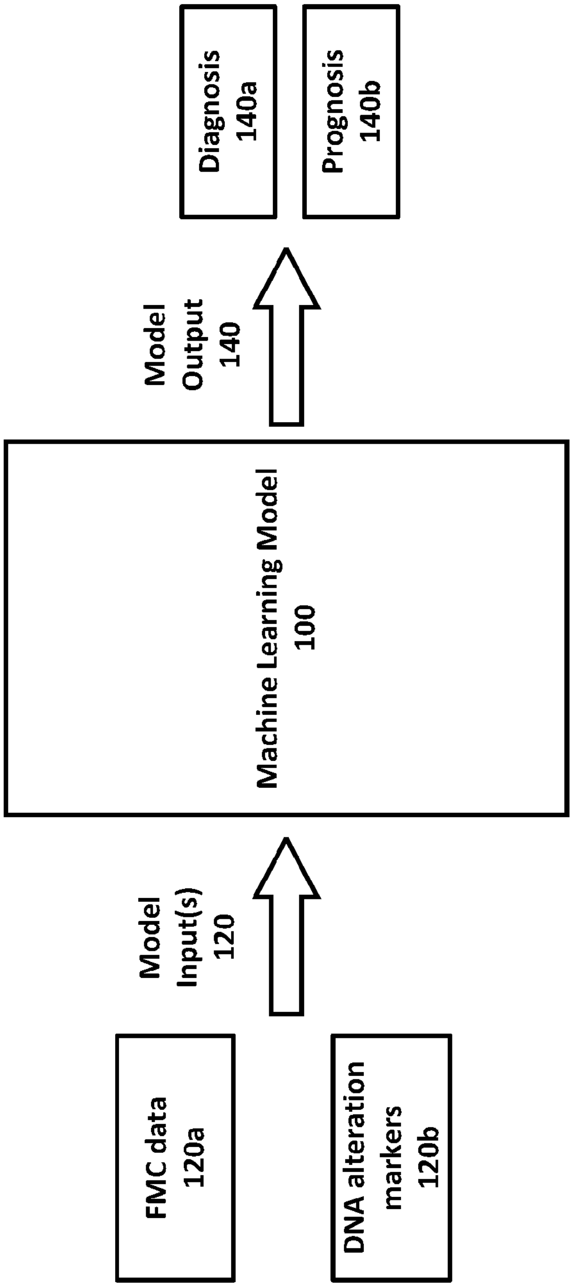
FIG. 1 is a block diagram of a trained machine learning model for predicting hematological conditions operating in inference mode according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "about" or "approximately" when referring to a measurable value such as an amount, a percentage, and the like, is meant to encompass variations of ±20%, ±10%, ±5%, or ±1% from the measurable value.

"Administration" of "administering" to a subject includes any route of introducing or delivering to a subject an agent. Administration can be carried out by any suitable means for delivering the agent. Administration includes self-administration and the administration by another.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The term "artificial intelligence" is defined herein to include any technique that enables one or more computing devices or comping systems (i.e., a machine) to mimic human intelligence. Artificial intelligence (AI) includes, but is not limited to, knowledge bases, machine learning, representation learning, and deep learning. The term "machine learning" is defined herein to be a subset of AI that enables a machine to acquire knowledge by extracting patterns from raw data. Machine learning techniques include, but are not limited to, logistic regression, support vector machines (SVMs), decision trees, random forest classifiers, and artificial neural networks. The term "representation learning" is defined herein to be a subset of machine learning that enables a machine to automatically discover representations needed for feature detection, prediction, or classification from raw data. Representation learning techniques include, but are not limited to, autoencoders. The term "deep learning" is defined herein to be a subset of machine learning that that enables a machine to automatically discover representations needed for feature detection, prediction, classification, etc. using layers of processing. Deep learning techniques include, but are not limited to, artificial neural network or multilayer perceptron (MLP).

Machine learning models include supervised, semi-supervised, and unsupervised learning models. In a supervised learning model, the model learns a function that maps an input (also known as feature or features) to an output (also known as target or targets) during training with a labeled data set (or dataset). In an unsupervised learning model, the model learns patterns (e.g., structure, distribution, etc.) within an unlabeled data set. In a semi-supervised model, the model learns a function that maps an input (also known as feature or features) to an output (also known as target or target) during training with both labeled and unlabeled data.

Referring now to FIG. 1, a block diagram of a trained machine learning model 100 for predicting hematological conditions is shown. In FIG. 1, the machine learning model 100 is operating in inference mode. The machine learning model 100 has therefore been trained with a data set (or "dataset") and is configured to make predictions based on new input data. Accordingly, such a model is sometimes referred to herein as a "trained machine learning model" or a "deployed machine learning model." In some implementations, the machine learning model 100 is a supervised machine learning model. Supervised machine learning models include, but are not limited to, random forest classifiers, support vector machines, Naïve Bayes classifiers, and artificial neural networks. It should be understood that random forest classifiers, support vector machines, Naïve Bayes classifiers, and artificial neural networks are provided only as example supervised machine learning models. This disclosure contemplates that the trained machine learning model 100 can be other supervised learning models. Additionally, it should be understood that supervised machine learning models are provided as an example.

As described above, a supervised machine learning model "learns" a function that maps an input 120 (also known as feature or features) to an output 140 (also known as target or targets) during training with a labeled data set. Machine learning model training is discussed in further detail below. In some implementations, a trained supervised machine learning model is configured to classify the input 120 into one of a plurality of target categories (i.e., the output 140). In other words, the trained model can be deployed as a classifier. In other implementations, a trained supervised machine learning model is configured to provide a probability of a target (i.e., the output 140) based on the input 120. In other words, the trained model can be deployed to perform a regression.

Optionally, in some implementations, the machine learning model 100 is a random forest classifier. A random forest classifier is a supervised classification model that uses a series of decision tree classifiers. This disclosure contemplates that the Random Forest classifier can be implemented using a computing device (e.g., a processing unit and memory as described herein). Random forest classifiers are trained with a data set by determining a decision in across connected nodes, where each node represents a feature of the data this results in a probability distribution of a label given an observation with sub-sampling of the data features. Random forest classifiers are known in the art and are therefore not described in further detail herein.

Optionally, in some implementations, the machine learning model 100 is a support vector machine (SVM). An SVM is a supervised learning model that uses statistical learning frameworks to predict the probability of a target. This disclosure contemplates that the SVM can be implemented using a computing device (e.g., a processing unit and memory as described herein). SVMs can be used for classification and regression tasks. SVMs are trained with a data set to maximize or minimize an objective function, for example a measure of the SVM's performance, during training. SVMs are known in the art and are therefore not described in further detail herein.

Optionally, in some implementations, the machine learning model 100 is a Naïve Bayes' (NB) classifier. An NB classifier is a supervised classification model that is based on Bayes' Theorem, which assumes independence among features (i.e., presence of one feature in a class is unrelated to presence of any other features). This disclosure contemplates that the NB classifier can be implemented using a computing device (e.g., a processing unit and memory as described herein). NB classifiers are trained with a data set by computing the conditional probability distribution of each feature given label and applying Bayes' Theorem to compute conditional probability distribution of a label given an observation. NB classifiers are known in the art and are therefore not described in further detail herein.

Optionally, in some implementations, the machine learning model 100 is an artificial neural network (ANN). An artificial neural network (ANN) is a computing system including a plurality of interconnected neurons (e.g., also referred to as "nodes"). This disclosure contemplates that the nodes can be implemented using a computing device (e.g., a processing unit and memory as described herein). The nodes can be arranged in a plurality of layers such as input layer, output layer, and optionally one or more hidden layers. An ANN having hidden layers can be referred to as deep neural network or multilayer perceptron (MLP). Each node is connected to one or more other nodes in the ANN. For example, each layer is made of a plurality of nodes, where each node is connected to all nodes in the previous layer. The nodes in a given layer are not interconnected with one another, i.e., the nodes in a given layer function independently of one another. As used herein, nodes in the input layer receive data from outside of the ANN, nodes in the hidden layer(s) modify the data between the input and output layers, and nodes in the output layer provide the results. Each node is configured to receive an input, implement an activation function (e.g., binary step, linear, sigmoid, tan H, or rectified linear unit (ReLU) function), and provide an output in accordance with the activation function. Additionally, each node is associated with a respective weight. ANNs are trained with a dataset to maximize or minimize an objective function. In some implementations, the objective function is a cost function, which is a measure of the ANN's performance (e.g., error such as L1 or L2 loss) during training, and the training algorithm tunes the node weights and/or bias to minimize the cost function. This disclosure contemplates that any algorithm that finds the maximum or minimum of the objective function can be used for training the ANN. Training algorithms for ANNs include, but are not limited to, backpropagation. ANNs are known in the art and are therefore not described in further detail herein.

As shown in FIG. 1, the machine learning model 100 is configured to provide output 140 based on the input 120. In the examples described herein, the input 120 includes fluctuating methylation clock (FMC) data 120*a* and optionally DNA alteration markers 120*b*, and the output 140 is a prediction of a hematological condition in the subject. The machine learning model 100 is therefore trained to map the input 120 to the output 140. In other words, the input 120 includes one or more "features" that are input into the machine learning model 100, which predicts the hematological condition (i.e., output 140) in the subject. The hematological condition in the subject is therefore the "target" of the machine learning model 100. Hematological conditions include, but are not limited to, clonal hematopoiesis (CH), clonal hematopoiesis of indeterminate potential (CHIP), and age related clonal hematopoiesis (ARCH). As described herein, the prediction (i.e., output 140) can be a diagnosis 140*a* of the hematological condition or a prognosis 140*b* of the hematological condition. It should be understood that a diagnosis and prognosis of a hematological condition are provided only as example predictions. This disclosure contemplates that the prediction may be different than the examples.

Figure 2:
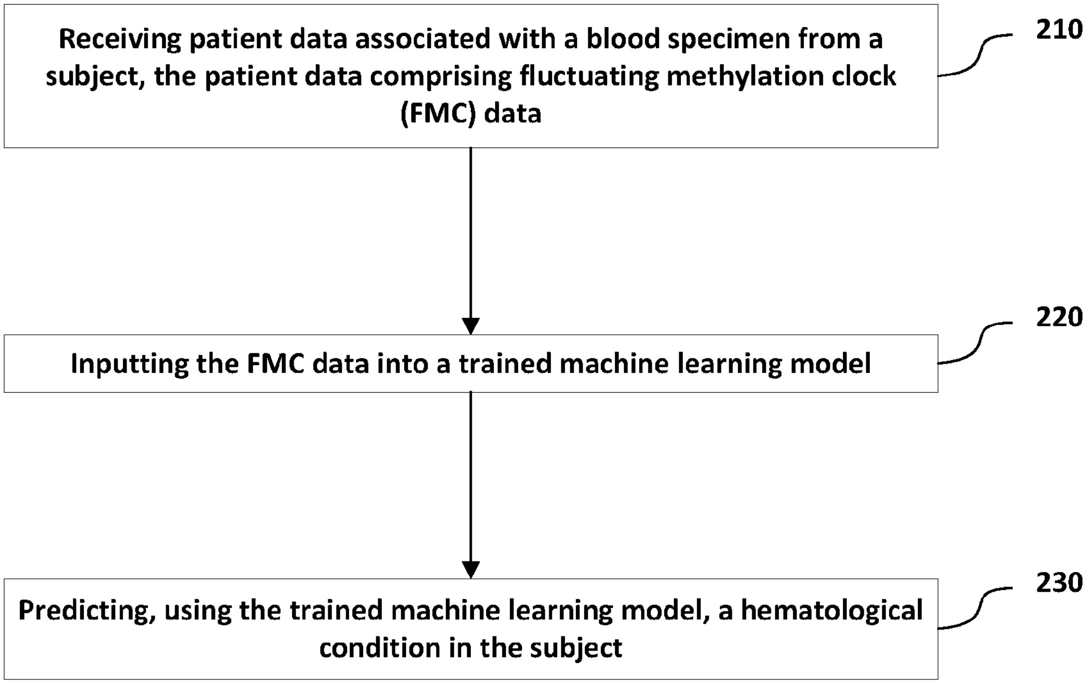
FIG. 2 is a flowchart illustrating example operations for predicting hematological conditions according to implementations described herein.

Referring now to FIG. 2, a flowchart illustrating example operations for predicting hematological conditions is shown. It should be understood that the logical operations of FIG. 2 can be performed using a computing device (e.g., the computing device of FIG. 3).

At step 210, patient data associated with a blood specimen from a subject is received, for example by the computing device. The patient data includes fluctuating methylation clock (FMC) data, where the FMC data includes deoxyribonucleic acid (DNA) methylation fluctuation data for a plurality of fluctuating CpG (fCpG) sites. CpG sites are regions of DNA where a cytosine nucleotide occurs next to a guanine nucleotide in the linear sequence of bases along its length. Thus, as used herein, "CpG" refers to cytosine and guanine separated by a phosphate, which links the two nucleosides together in DNA. As described herein, fluctuating DNA methylation marks can be used as clocks in cells where ongoing methylation and demethylation causes repeated cycling between methylated and unmethylated states. In particular, CpG sites stochastically and measurably fluctuate in their DNA methylation levels (specifically the fraction of methylated alleles, typically referred to as the β value) between 0% (homozygously unmethylated CpG), 50% (heterozygous methylation) and 100% (homozygous methylation).

In some implementations, the blood specimen is optionally a peripheral blood sample extracted from the subject. DNA can be extracted from such blood specimen and DNA methylation can then be measured, for example, using a microarray. Example microarrays for measuring DNA methylation include, but are not limited to, EPIC microarrays from Illumina, Inc. of San Diego, California. Techniques for extracting DNA, isolating DNAs, and analyzing DNAs with a microarray are known in the art. As described above, the FMC data includes DNA methylation fluctuation data for a plurality of fCpG sites. It should be understood that the FMC data includes DNA methylation fluctuation data for specific fCpG sites. Optionally, as described in the Examples below, the specific fCpG sites can include all CpG loci having average values between 40% and 60% methylation in a dataset (e.g., the aging database of 656 healthy individuals discussed in Example 1). It should be understood that specific fCpG sites used for predicting hematological conditions using blood specimens may be different than fCpG sites used for predicting diseases using other tissue samples or fCpG sites used for predicting other diseases. Additionally, it should be understood that a peripheral blood sample is only provided as an example blood specimen. This disclosure contemplates that the blood specimen can be a skeletal bone marrow sample in other implementations.

Optionally, in some implementations, the patient data further includes one or more DNA alteration markers. For example, the one or more DNA alteration markers can include, but are not limited to, a single nucleotide variant (SNV), a copy number alteration (CNA), or a structural variant (SV). DNA alteration markers can be obtained by sampling the subject's blood, extracting DNA from the sample, sequencing the DNA, and identifying DNA alteration markers in the data. DNA alteration markers can be identified based on a comparison of the blood sample DNA sequences to a control set of DNA sequences derived from a control subject or population that either has no disease or no disease recurrence. Techniques for extracting DNA, isolating DNAs, and sequencing are known in the art.

At step 220, the FMC data is input into a trained machine learning model (e.g., machine learning model 100 in FIG. 1). In some implementations, the trained machine learning model is a supervised machine learning model such as a random forest classifier. It should be understood that a random forest classifier is provided only as an example. This disclosure contemplates that the trained machine learning model is a different type of supervised machine learning model including, but not limited to, SVMs and ANNs. Optionally, in some implementations, the FMC data and one or more DNA alteration markers are input into the trained machine learning model (e.g., machine learning model 100 in FIG. 1) at step 220.

At step 230, the trained machine learning model (e.g., machine learning model 100 in FIG. 1) predicts a hematological condition in the subject. In some implementations, the step of predicting, using the trained machine learning model, the hematological condition includes diagnosing the subject with the hematological condition. In some implementations, the step of predicting, using the trained machine learning model, the hematological condition includes providing a prognosis of the hematological condition. Alternatively or additionally, the hematological condition may be clonal hematopoiesis (CH), clonal hematopoiesis of indeterminate potential (CHIP), or age related clonal hematopoiesis (ARCH).

In some implementations, the techniques described herein relate to a method including: receiving a blood specimen from a subject; obtaining, using a microarray, fluctuating methylation clock (FMC) data associated with the blood specimen; and inputting, using a computing device, the FMC data into a trained machine learning model; and predicting, using the trained machine learning model, a hematological condition in the subject. In some implementations, the method further includes recommending, using the computing device, a course of treatment for the subject based on the predicted hematological condition. In some implementations, the method further includes recommending performing a course of treatment on the subject based on the predicted hematological condition.

It should be appreciated that the logical operations described herein with respect to the various figures may be implemented (1) as a sequence of computer implemented acts or program modules (i.e., software) running on a computing device (e.g., the computing device described in FIG. 3), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 3:
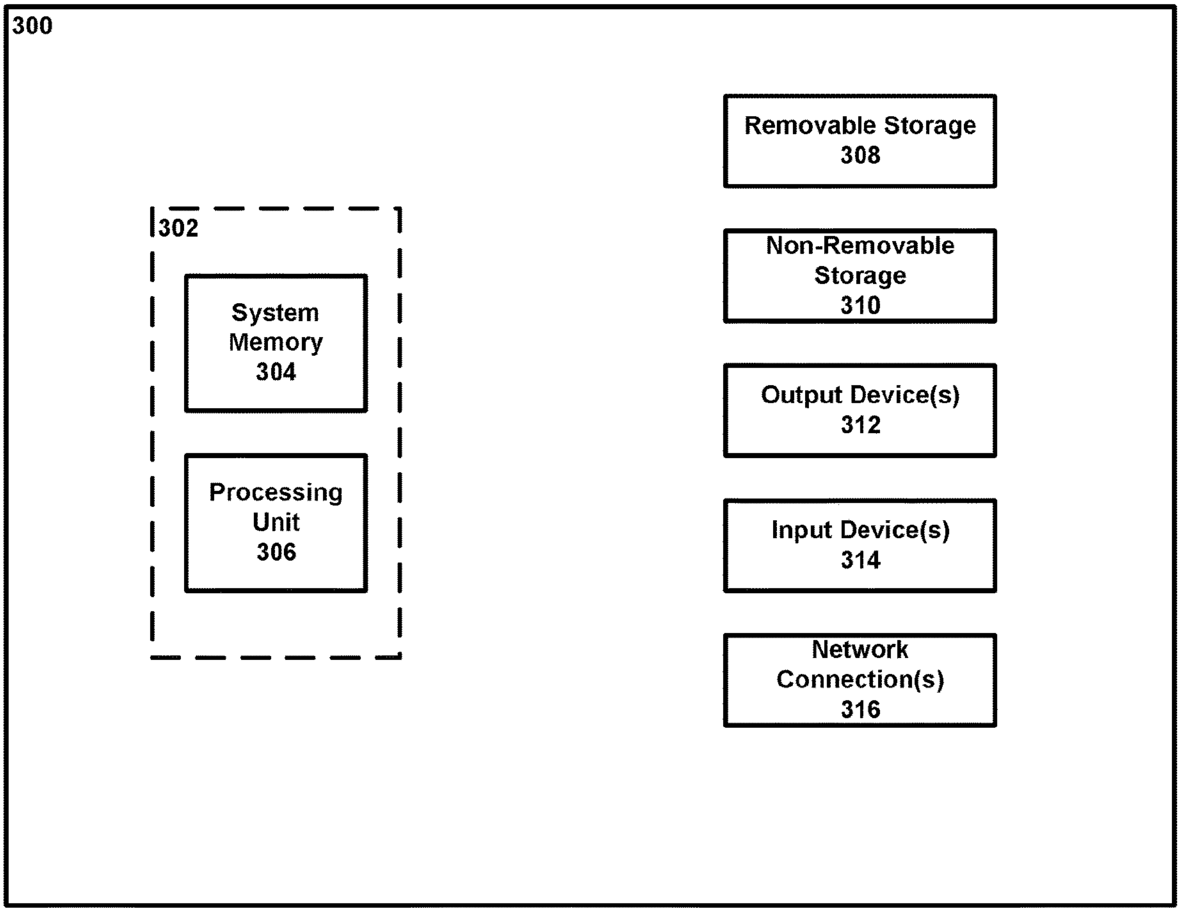
FIG. 3 is an example a computing device.

Referring to FIG. 3, an example computing device 300 upon which the methods described herein may be implemented is illustrated. It should be understood that the example computing device 300 is only one example of a suitable computing environment upon which the methods described herein may be implemented. Optionally, the computing device 300 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by box 302. The processing unit 306 may be a standard programmable processor that performs arithmetic and logic operations necessary for operation of the computing device 300. The computing device 300 may also include a bus or other communication mechanism for communicating information among various components of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Tangible, computer-readable media refers to any media that is capable of providing data that causes the computing device 300 (i.e., a machine) to operate in a particular fashion. Various computer-readable media may be utilized to provide instructions to the processing unit 306 for execution. Example tangible, computer-readable media may include, but is not limited to, volatile media, non-volatile media, removable media and non-removable media implemented in any method or technology for storage of information such as computer readable instructions, data structures, program modules or other data. System memory 304, removable storage 308, and non-removable storage 310 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

We previously discovered and exploited FMCs to determine the stem cell numbers and replacement rates in various healthy and precancerous glandular tissues. Within the colon crypts and endometrium glands regular monoclonal conversions occur via neutral drift over a predictable period in healthy and pre-malignant tissue due to their small numbers of stem cells and spatially confined organization. This differs from the hematopoietic system where polyclonality of the hematopoietic stem cell (HSC) population is extensive and clonal expansions are only likely in the most severe malignancies due to the multiple orders of magnitude more stem cells in a spatially unstratified tissue. The fCpG behavior seen in intestinal crypts and endometrial glands (both epithelium tissues) are likely to be present across other tissue types.

Figure 4:
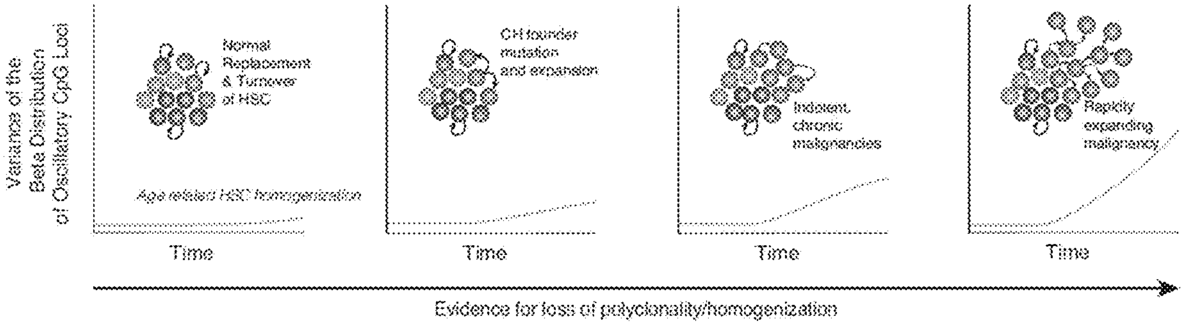
FIG. 4 illustrates fluctuating methylation clock idealization in whole blood. Illustration of a diverse HSC compartment with normal turnover and fluctuating CpG (fCpG) variances. Through several possible routes the variances move from the normal, steady state at 50% to the "W" like distribution seen in the crypt in the most extreme, rapidly expanding malignancies. Various stages of hematopoietic stem cell (HSC) homogenization is reflected in the fCpG variances.

As described in this example, the loss of polyclonality, or homogenization of the HSC pool, should be reflected in fCpG distributions of normal, pre-malignant, and malignant samples (FIG. 4). This idea is easily explored through abundant publicly available datasets. Unlike intestinal crypts which recurrently drift to clonality, blood is a large, well-mixed tissue with diverse cell types and is normally polyclonal because it is produced by thousands of bone marrow stem cells. Normal HSC turnover is not synchronized. As in the intestines, CpG loci that randomly fluctuate through 0%, 50% and 100% methylation in individual cells will have average methylation around 50% in normal polyclonal blood samples.

Here, we build a mechanistic HSC model to show, through symmetric divisions, how fCpG variance increases as polyclonality is lost. We turn to the abundant public methylation array datasets for normal, pre-malignant, and malignant whole blood samples to derive fCpG sites. Unlike the crypt, a separate, less refined, identification process is necessary as heterogeneity of CpG 6 values is inaccessible within patients due to a lack of measurements within the same individual. Unfortunately, no methylation array datasets currently exist for CH. We collect and analyze 38 patients whole blood samples who have paired methylation array and mutation data, from paired peripheral blood (PB) and bone marrow (BM), with confirmed CH along with ten confirmed normal control samples. Using this cohort, we develop a novel approach to diagnose CH agnostic to mutation status, evaluating evidence of CH in 1,388 patients.

Hematopoiesis Model

Whole blood was simulated in Java using the HAL framework as a non-spatial agent-based model using 27, 634 fCpG sites as measured in the experimental data. Parameters for normal hematopoiesis are numbers of HSCs (N), number of possible division events (T), (de)methylation rates (S) for the fCpG sites, and HSC replacement dynamics (λ). To model clonal expansion, a single, random, cell was selected to grow upon induction, and added parameters are its expansion rate (E) and its final blood frequency of the clonal expansion (ω). These clonal expansions resulted in the overall population size to grow until the appropriate final blood frequency was reached. The output of the simulations provided the β values at the fCpG sites and the overall distribution variance over time.

The number of HSCs was set at a lower value of 1000 initiating cells. This was much lower than the 30,000 based on the large number of HSC inferred by DNA sequencing studies; however, the results shown here are invariant to more than 100 initiating cells. (De)methylation rates varied between CpG sites and were assigned based on the distribution averages of the 656 normal, healthy, individuals from GSE40279. We found that some of the whole blood fCpGs did not appear to have equal (de)methylation rates because their averages tended to always be above or below 50% in multiple individuals. Hence, to better model and match the data, we used a look-up distribution table in the simulations to initialize a cell's fCpG parameters, with lower and unequal (de)methylation rates at CpG sites with average methylation typically found near 0.4 (demethylation> methylation) or near 0.6 (methylation>demethylation) to maintain the variance of the 27,634 fCpG sites around 0.1 during cell divisions. The (de)methylation rates varied between 0.0001 to 0.001 changes per division, with the highest (de)methylation rates and more equal (de)methylation rates at CpG sites near 50% methylation.

Figure 5A:
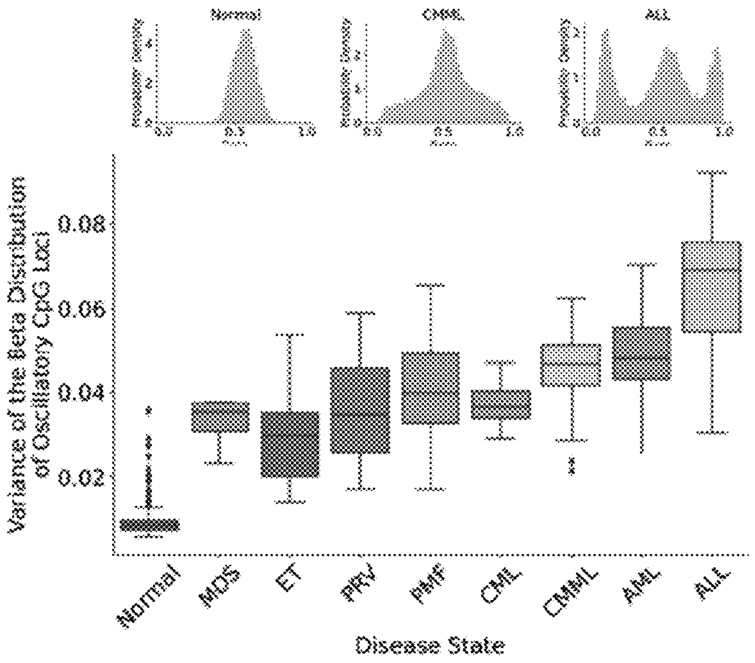
FIGS. 5A-5F illustrate fluctuating CpG dynamics can be observed in chronic and acute leukemia.
Figure 5B:
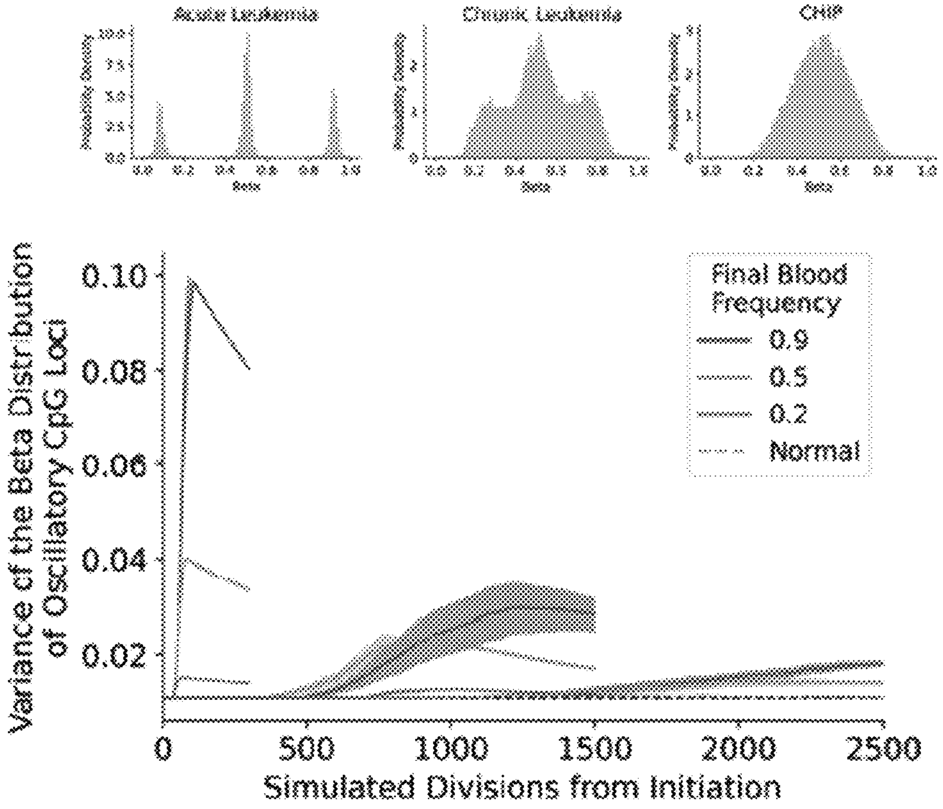

Cell survival was set at exact replacement (one cell produces one living offspring), and results did not vary much if random replacement was simulated. A proportion of cells underwent replacement at each timestep. For the neoplastic simulations in FIG. 5D the expansion rate (E) was varied to model either rapid expansion (visible or more than 5% leukemic cells within 1 year or 200 divisions) akin to acute leukemia, modest expansion (visible within 4 years or 12,000 divisions), or very slow expansion (visible within 6 years or 18,000 divisions). The extent of blood involvement was varied between 20% (black lines), 50% (blue lines) and 90% (red lines). These simulations indicated that how clonal expansions change whole blood fCpG variances depends both on how fast the expansion grows and to what extent it involves the blood. Rapid growth to high levels like acute leukemias results in high fCpG variances and characteristic W-shaped fCpG distributions. Slower growth to lower levels like chronic leukemias results in low fCpG variances and broader distributions that lack the W-shape. Interestingly, very indolent clonal expansions which may occur with CH can result in small increases in fCpG variances, which may account for the age-related increase in fCpG variances seen in FIG. 5A.

More sophisticated modelling with a better selection of whole blood fCpG sites could improve the extraction of ancestral information. For example, a selection of slower fCpG sites may improve the detection and analysis of indolent clonal expansions, where many of the faster fluctuations return to average ~50% methylation by the time the expansion reaches detectable blood levels.

Fluctuating Methylation Clock Dynamics in Hematopoiesis Simulations

We simulated hematopoiesis to better understand how fluctuating sites detect clonality in whole blood (FIGS. 5A-F). Methylation fluctuates between 0%, 50% and 100% in single cells and the simulations indicate polyclonal whole blood variance is low and stable through time because human hematopoiesis is maintained by large numbers of stem cells. Clonal expansion by a single cell synchronizes fluctuations and results in higher whole blood variances that depend on growth rates. As in the crypts, there is a balance between clonal expansion rates, which increase population variances, and the rates at which fluctuating sites drift back to 50% average methylation, which decreases variance. A rapid expansion (less than 2 years) to high blood levels as in acute leukemias produces high variances and W-shaped distributions. The "W" methylation pattern resembles the methylation at 0, 50 and 100% methylation of the initiating cell. Expansions that grow more slowly have variances greater than normal blood but lack the W-shape as methylation fluctuations become increasing desynchronized with time. These more indolent expansions are more consistent with the experimental data for chronic myeloproliferative neoplasms, which may be asymptomatic and persist for years. Clones that grow even slower and arise later, as may occur with age related CH, leads to slightly higher variances, as seen with aging in the normal whole blood cohort. Hence, a simple model with 27, 634 fCpG sites and different rates of clonal expansion is broadly consistent with the experimental data from hundreds of clinical samples.

Fluctuating CpGs in Publicly Available Blood Samples

Figure 5C:
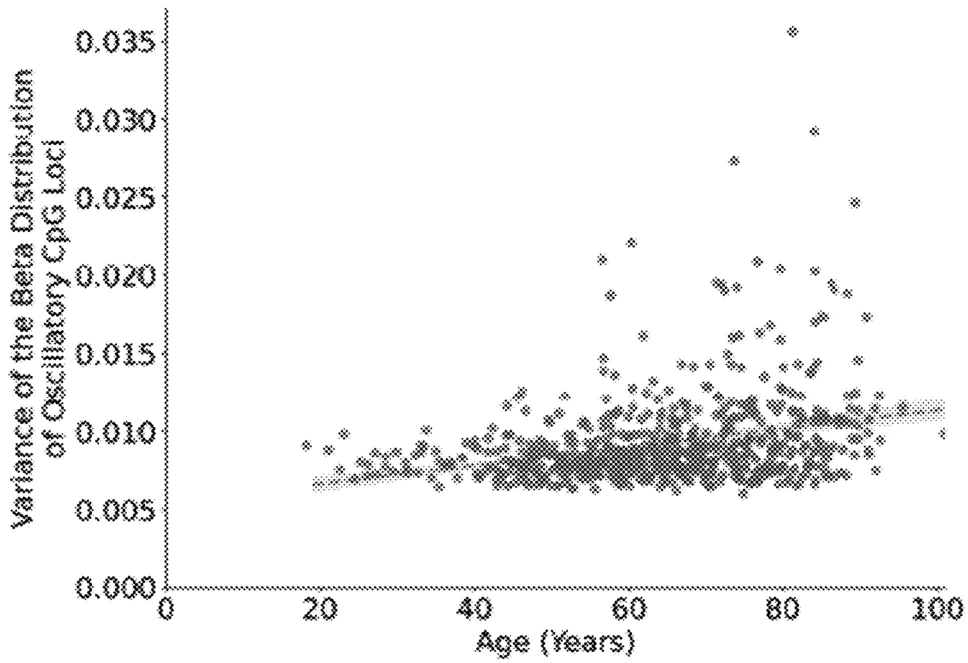
Figure 5D:
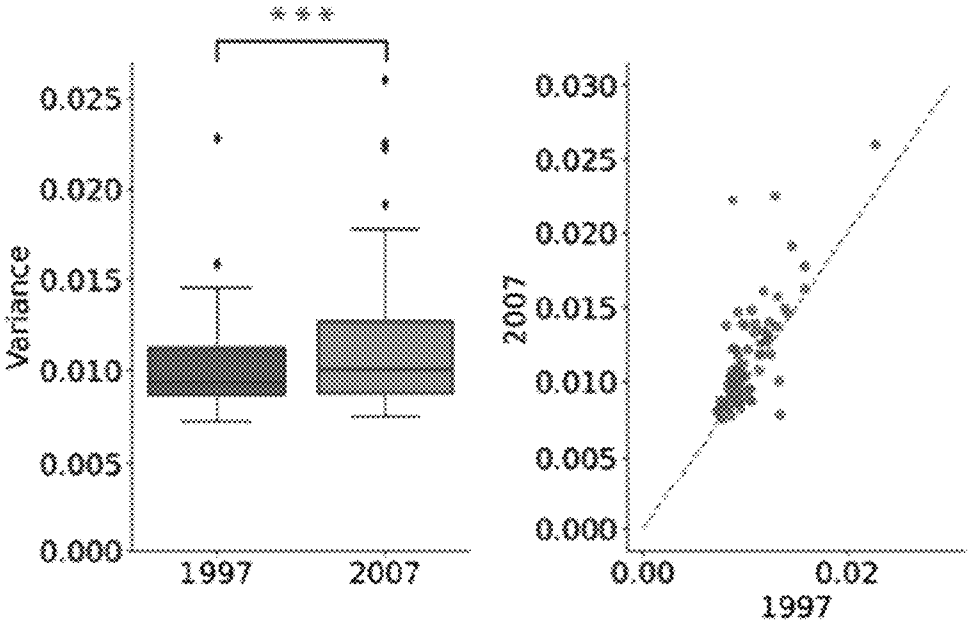
Figure 5E:
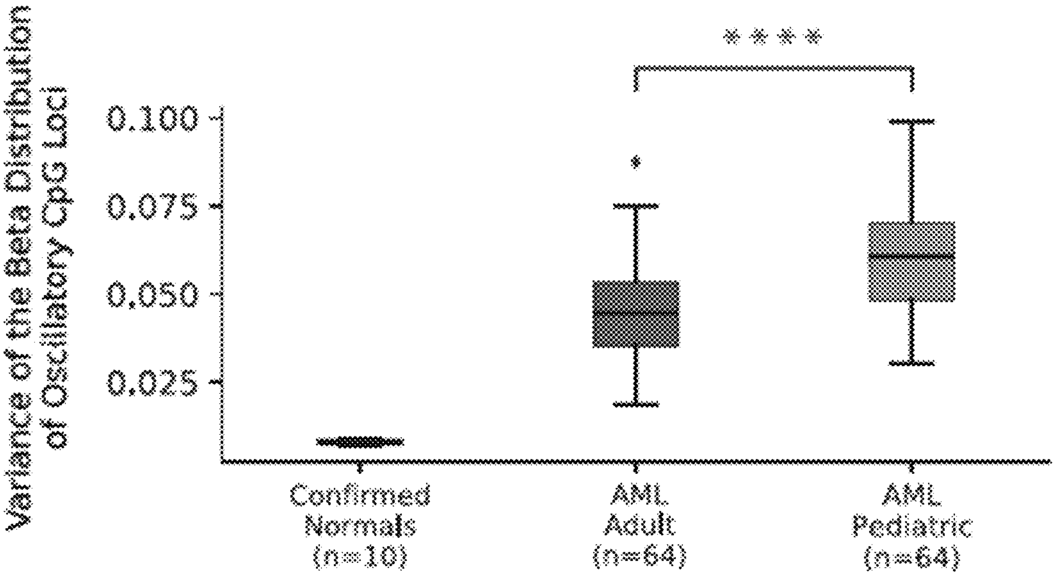
Figure 5F:
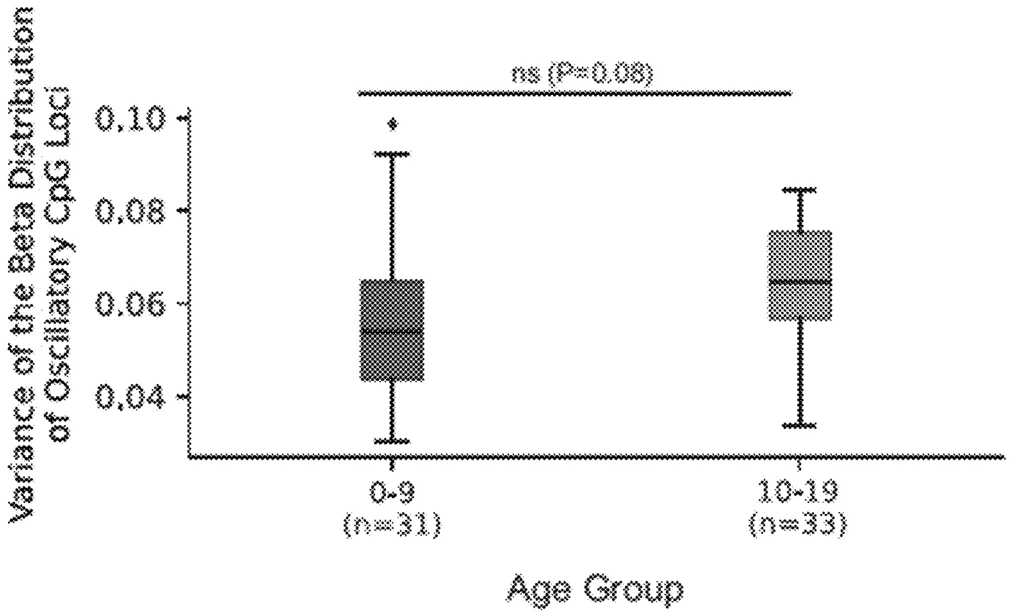

We identified suitable fCpG loci by averaging normal whole blood DNA methylation at ~450,000 autosomal CpG loci from a commonly used aging database of 656 healthy individuals. We selected all loci (N=27, 634) with average values between 40 and 60% methylation in these 656 specimens. fCpG appear tissue-specific because only ~5% of the intestinal loci were in the blood set. Fluctuating methylation for each individual sample revealed tight distributions around 50% methylation, which can be described by its variance (FIG. 5C). Consistent with random fluctuations, average fluctuating methylation remained 50% with aging. Serial samples ten years apart revealed variance to be relatively stable for an individual, with a slight significant trend for increases with age (FIG. 5D), which was also observed throughout aging (FIG. 5C). HSCs start out homogenous and expand, introducing mutations and individual lineages until patients are approximately 20 years old. We observe this in the fCpG variance in two AML cohorts where a predominantly older cohort (70.3% over the age of 50; GSE62298) exhibits significantly lower fCpG variance compared to the pediatric AML cases, all under the age of 18 (n=64; GSE133986) (FIG. 5E). HSC homogenization is more exaggerated within these pediatric samples in early HSC homeostatic development.

CH in the blood is an early step in the evolution of neoplasia and will increase variances because clonal cells will initially share the 0, 50, 100% methylation pattern of the progenitor. For rapid clonal expansions (i.e., acute leukemias), W-shaped blood distributions like those observed in the crypts are expected. Consistent with these expectations, whole blood samples from different types of major hematopoietic neoplasm had higher than normal variances (FIG. 5A). Acute lymphoblastic leukemias (ALL) and acute myeloid leukemias (AML) had the highest variances and characteristic W-shaped distributions. More indolent chronic myeloproliferative or myelodysplastic whole blood specimens showed more modest variance increases and generally lacked the "W" shape of the acute leukemias, crypts and glands.

Clonal Hematopoiesis

Clonal hematopoiesis (CH) is diagnosed based on somatic alterations whose frequencies are greater than 2% (generally SNVs and small insertions and deletions assessed from peripheral blood samples) in the absence of hematologic malignancy. The prevalence of CH increases as an individual ages and conveys a non-negligible risk for progression to various hematopoietic malignancy. While these studies focus on specific somatic alterations, there are others that have more generally found an increased risk of hematologic malignancies by defining CH as samples with high numbers of somatic mutations. Further still, chromosomal anomalies such as large structural variants or CNAs are also associated with increased risk of hematopoietic malignancies, but are not generally defined as a diagnostic method for CH, despite their more common occurrence in individuals who subsequently develop myeloid or lymphoid leukemia, as observed through longitudinal studies. While these risks for all somatic alterations carry an increased risk of developing malignancies, the absolute risk is low; however, incorporating a more broadly universal method for identifying CH is of great value, especially if information could be gained for teasing apart risk for hematopoietic malignancies. Here we develop a method agnostic to the underlying somatic alteration type by using FMC behavior.

Clonal Hematopoiesis Patient Cohort

Figure 6A:
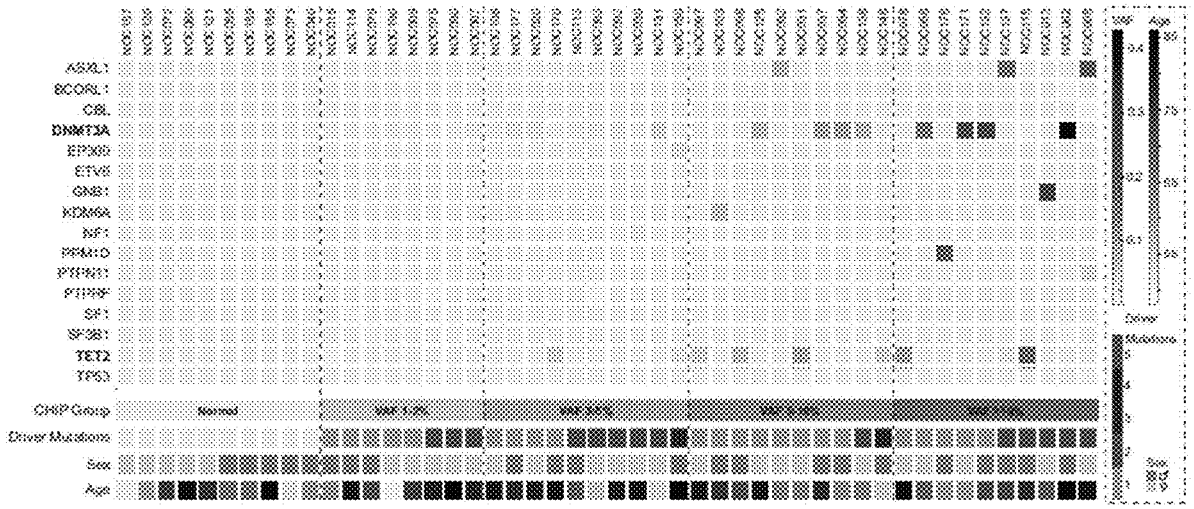
FIGS. 6A-6C illustrate characterization of CH patient samples.
Figure 6B:
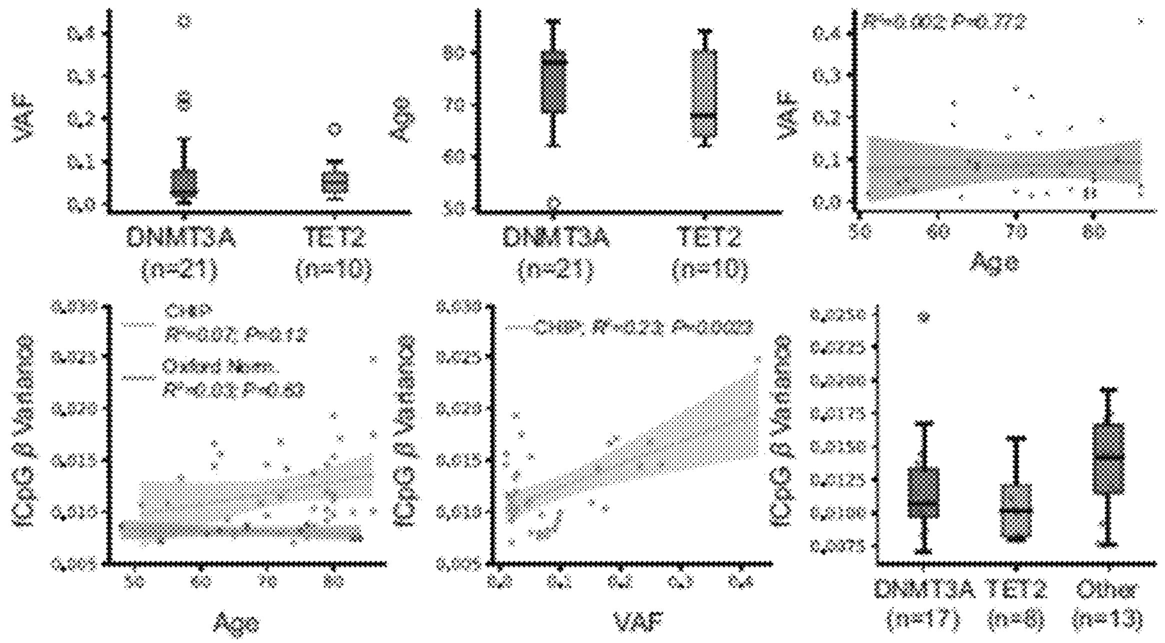

Patients undergoing elective total hip replacement surgery were diagnosed as either normal or CH based on the VAF of putative driver mutations. Here, we present ten patients with no evidence of CH and 38 patients subdivided into different VAF groups ([1,2) % n=8, [2,5) % n=10, [5,10) % n=10, 2: 10% n=10) whose VAF of putative drivers is greater than 1%. Most patients present with a DNMT3A driver mutation (21/38 (about 55%) CH patients), where ≈81% (17/21) of those DNMT3A drivers are the highest frequency driver mutation for that patient. TET2 is the second most frequently observed driver, (10/38 (≈26%) CH patients), where 8/10 (≈80%) TET2 drivers are the highest frequency driver mutation for that patient (FIG. 6B). A smattering of additional driver mutations are observed, such as ASXL1 (n=5), TP53 (n=2), and SF3B1 (n=3). We don't observe any significant differences between the predominant driver mutations (DNMT3A and TET2) for their corresponding variant frequencies or patient ages (P=0.76 and P=0.17, respectively, two-sided Welch's t-test, FIG. 6D). In addition, there is no significant increase in the observed VAF of driver mutations with age (FIG. 6D). Together, this supports those mutations are expanding at a steady rate corresponding to their time of induction.

Figure 6C:
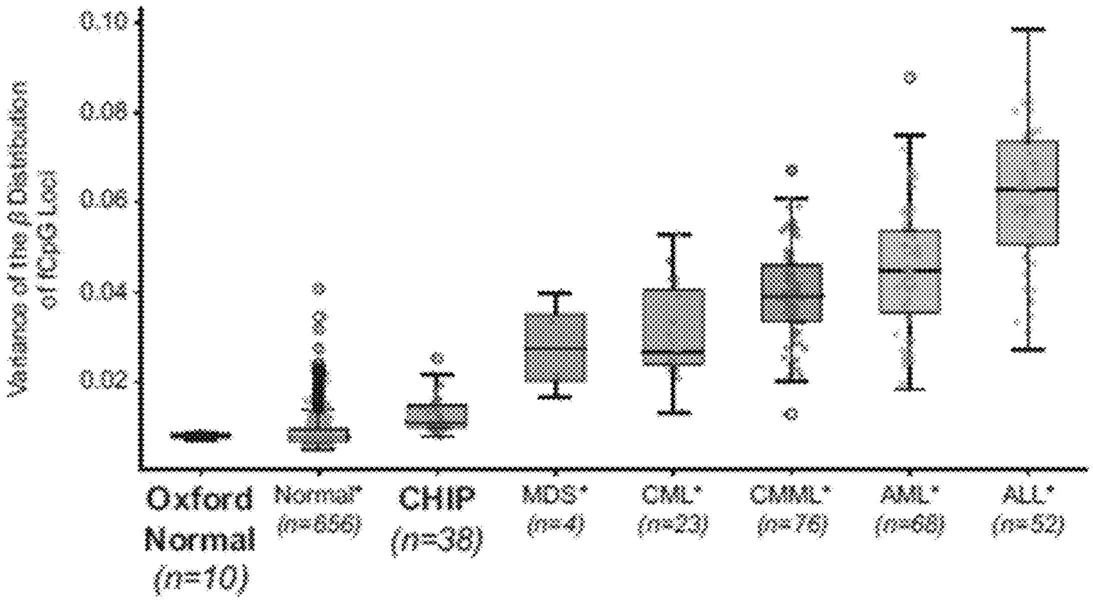

Clonal Hematopoiesis Fluctuating Methylation Clocks fCpG in the blood form a predictable distribution around 50% methylation in normal samples (FIG. 5A and FIG. 6C), as founder mutations leading to CH or mutagenesis increases the variance of these fCpG methylation sites as evidence for loss of polyclonality or homogenization occurs; where we expect to see fCpG sites concentrated at 0%, 50%, and 100% methylation. Consistent with these findings we see that the mean variance for the control samples, confirmed normal is $8.1*10^{-3}\pm5.7*10^{-4}$ (mean±SD, n=10) while the mean variance for the CH samples is 0.012±3.8*10 (mean±SD, n=38). Normal samples taken from GEO exhibit a similar mean, but the distribution of fCpG variance has a left skew towards loss of polyclonality as reflected in a higher standard deviation ($8.9*10^{-3}\pm3.7*10^{-3}$, mean±SD; n=656); however, low frequency CH driver mutations cannot be ruled out for this sample group as paired mutational data was not collected. The next highest fCpG variance, at an order of magnitude higher, are in malignant samples for MDS ($0.028\pm9.0*10^{-3}$ mean±SD; n=4) and CML (0.031±0.01 mean±SD; n=23). Recent work has shown that 92.4% of clones expand steadily with slow exponential expansions after driver acquisition, primarily for TET2 and DNMT3A mutations. In support of this, we expect and observe no differences between fCpG variances for TET2 and DNMT3A ($0.012\pm4.0*10^{-3}$ and $0.011 \pm 2.9*10^{-3}$ mean±SD, respectively) driver mutations (two-sided Welch's t-test, P>0.05; FIG. 6C). We do see a slight increase in fCpG variances for other driver mutations who are expected to expand rapidly, but there are insufficient numbers of these drivers to draw definitive conclusions from this dataset.

Mutation Agnostic Tool for Diagnosing Clonal Hematopoiesis

Figure 7A:
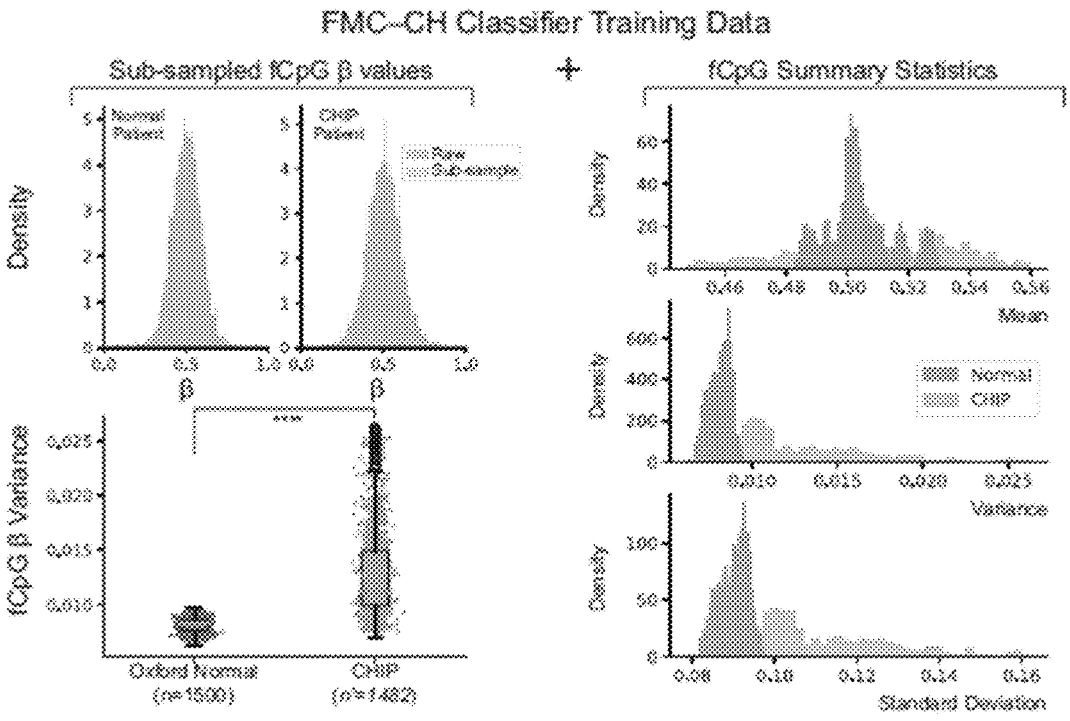
FIG. 7A-7E describe an FMC-CH classifier.
Figure 7B:
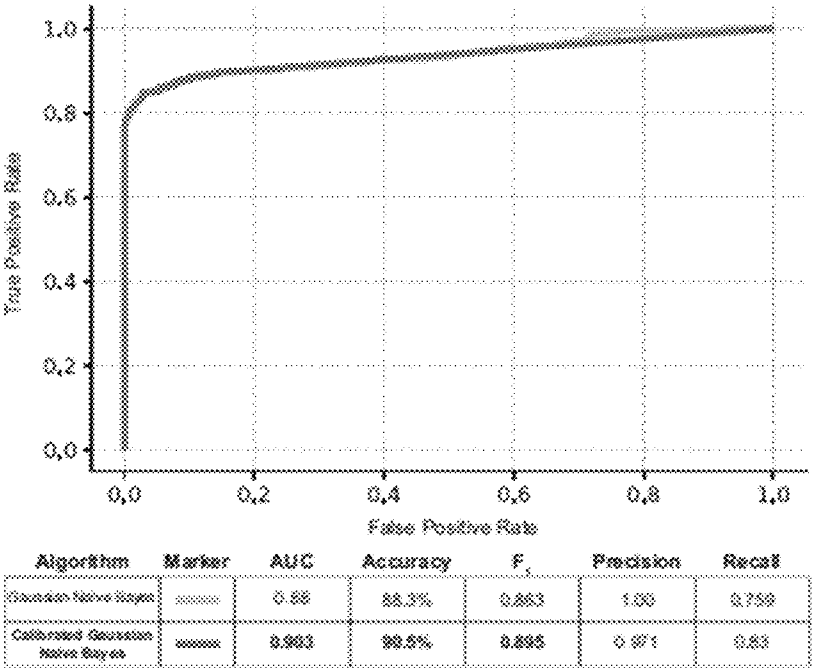

To evaluate whether CH can be diagnosed using fCpG sites we used our cohort of confirmed CH and normal samples. Publicly available normal methylation data does not have any paired mutational data to rule out the presence of CH in the study's cohort of patients, especially patients with early CH where clones would be observed only at very low frequencies. Here we sub-sampled our 12,000 fCpG sites, without replacement, to bolster our numbers of samples to roughly 1500 samples of both Normal and CH (1500 and 1482, respectively). Each patient is sub-sampled equally so that representation from each sample is equal across our normal and CH VAF groups. This leaves us with 2982 samples of roughly equal representation from normal and CH samples (FIG. 7A). In addition to the 2000 fCpG sites sampled to create each sub-sample, three summary statistics for each sub-sample (mean, variance, and standard deviation) is used to bolster our predictive power (FIG. 7A). We perform a train/test split of 80%/20% for these samples and train an ensemble random forest classifier supervised learning algorithm to classify our samples as either CH or normal. The algorithm is trained using a five-fold cross validation scheme with prediction probabilities calibrated using non-parametric isotonic regression. This FMC-CH classifier is capable of differentiating CH and normal samples with an accuracy of 90.5% and an area under the receiver operating characteristic curve (AUC) of 0.903 (FIG. 7B). Additionally, the balanced F-score ($F_1$, balance in precision and recall where $$F_1 = 2 * \frac{\text{precision} * \text{recall}}{\text{precision} + \text{recall}}$$

for this classifier is 0.895 (FIG. 7B). In the absence of the calibration and five-fold cross validation (i.e., no isotonic regression) we see that the accuracy is very close at 88.3%, but the $F_1$ score is lower at 0.863 indicating a larger imbalance in precision and recall.

Classifier Performance on Clonal Hematopoiesis Patient Cohort

Figure 7C:
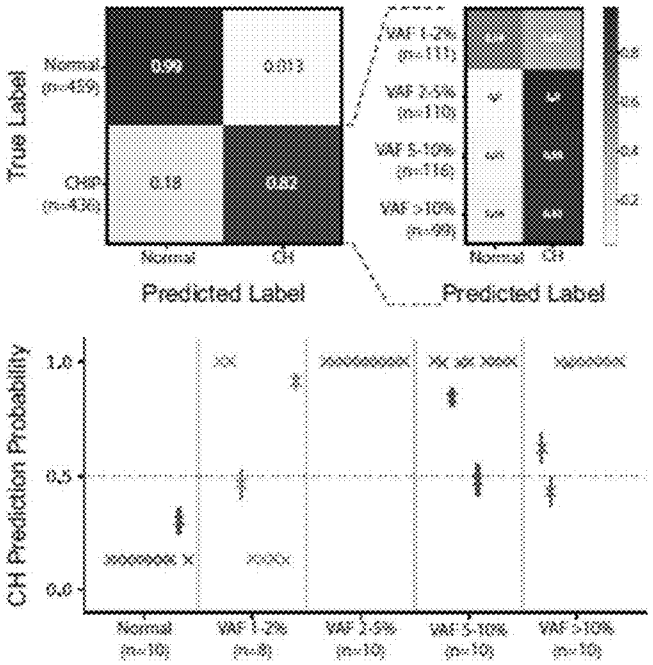

The FMC-CH classifier proves to be a robust tool for diagnosing CH based only on fluctuating methylation clocks. The confusion matrix between the normal and CH samples yields a false positive rate of only 1.8% and false negative rate of 8.2% (FIG. 7C). Our FMC-CH classification tool is a binary classifier where samples are either CH or normal. However, our CH cohort has been carefully curated for samples with known degrees of CH subclonal expansions, even those that are below clinical detection (<2% VAF). fCpG variance correlates with the VAF of CH drivers (FIG. 6B), thus we would expect that the classifier would struggle with sub-clinical CH samples. We evaluated how well the model performs across the different VAF groups by examining the true CH samples. When we pull these out of the confusion matrix, we can see that the lowest accuracy is for the CH group at 1-2% VAF where the false negative rate is 58% (FIG. 7C). Across the remaining groups the false negative rate does not exceed 8%.

A diagnostic or research tool is only useful with an appropriate interface and an easily integrated function. For the FMC-CH classifier a function is provided that takes an array of fCpG β values. The function pre-processes these samples, by performing the appropriate sub-sampling (allowing backwards compatibility with 450 k, 850 k, and earlier CpG probe sets), extracting the relevant summary statistics, and then performing the classification. This process is performed 100 times (by default, but the user can specify) providing summary statistics, such as a 95% confidence interval of the prediction probabilities. The threshold for CH classification from the replicate predictions is based on the 95% confidence interval, where CH is diagnosed if the upper limit of the 95% confidence interval is >50%. We illustrate this process by performing predictions on the entire CH cohort (FIG. 7C), revealing that samples with the smallest frequency CH driver clones are the most difficult to diagnose.

In-Silico Evaluation of Classification Model

Figure 7D:
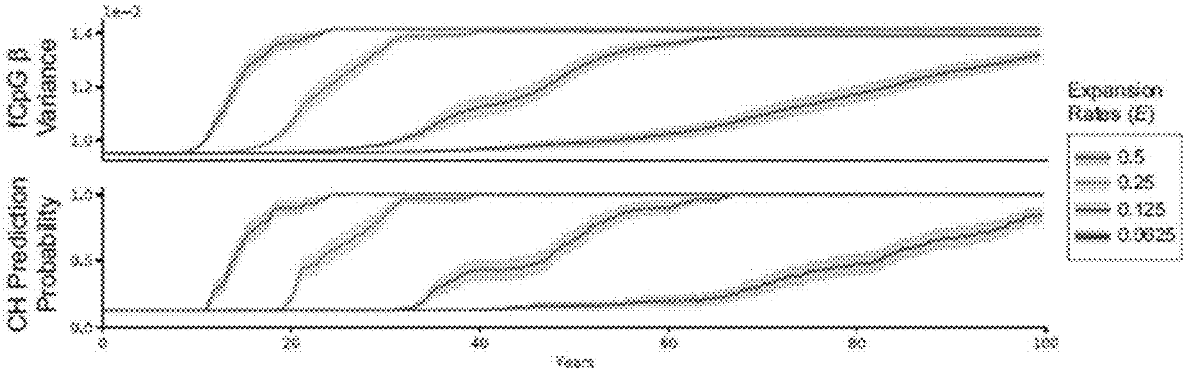
Figure 9A:
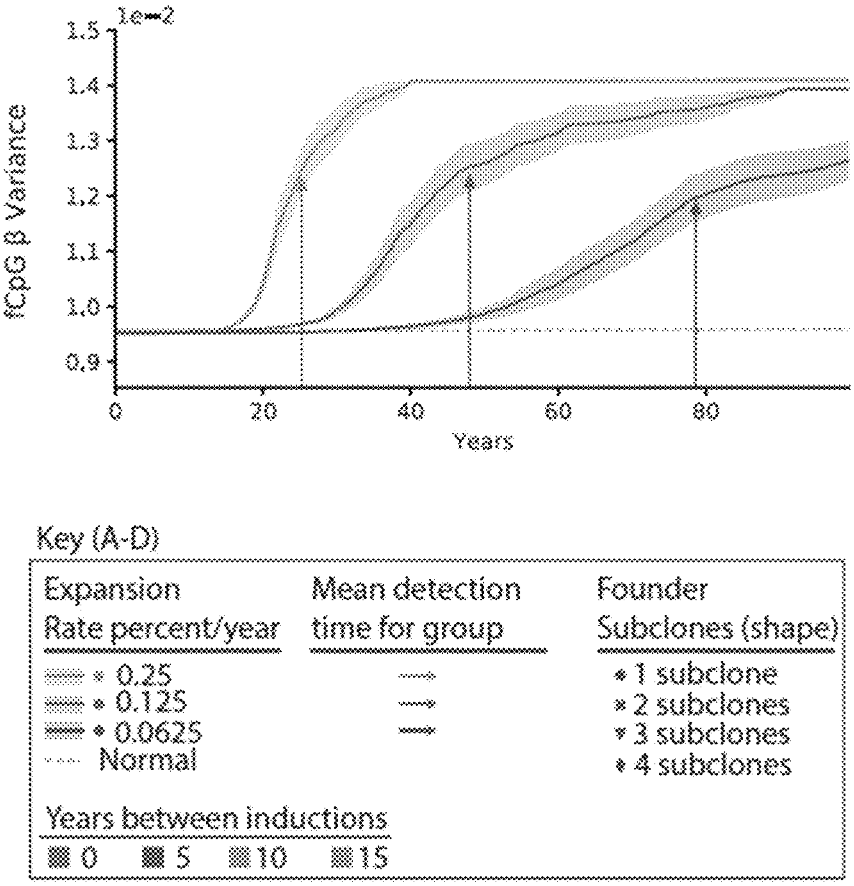
FIGS. 9A-9D illustrate concurrent driver mutations in the model.

The gold standard for identifying CH is through identification of deleterious somatic alterations from PB with a VAF cutoff of 2%. We know that FMC dynamics are a function of several underlying processes. At their core it is the turnover, cell number, expansion rates, (de)methylation rates, and final blood frequency of sub-clones/malignant populations FIG. 5B. Using our in silico model of HSC turnover and subclonal expansions we evaluated under what parameters the FMC-CH classifier may struggle to resolve CH status. The primary consideration for whether a growing subclone will be detected by the classifier is the rate of expansion. The rate of expansion, combined with the frequency of subclones, are the largest contributors to changes in the fCpG variance. Clones that expand with high rapidity results in the earliest detection using the FMC-CH classifier (FIG. 7D; 50 percent per year). How-ever, this steep increase in fCpG variance is similar to those seen in malignancies (FIG. 5B and FIG. 6C) where clonal frequencies are generally >>20%. Clones expanding slowly take much longer to reach a point where they are classified as CH, as the number of fCpG sites changing with the stem cell expansion are too few and remain 'hidden' in the fCpG β distribution maintaining, a distribution similar to the normal polyclonal HSCs fCpG β distributions (FIG. 5A and FIG. 5B). However, once these subclones have reached a high enough frequency, comparable to those that are seen in CH, the FMC-CH classifier accurately determines the presence of CH within simulations (FIG. 7D and FIG. 9A).

While the FMC-CH classifier can accurately determine that CH is present with increasing accuracy as a clone expands (FIG. 9C), there are differences in how soon the classifier reliably determines when CH is present based on the expansion rate of a clone. The gold standard for diagnosis of CH is based on a collection of different putative driver genomic alterations (SNVs as well as small insertions/deletions) that result in fitness advantages for that HSC population. Here we calculate a corresponding VAF likeness for a growing subclone within our HSC model to compare a gold standard VAF diagnosis with the FMC-CH classifier. This is accomplished using the method defining the depth, d, as 200 and defining $VAF_t$ for the expanding subclone as half its final blood frequency (assuming a heterozygous single clone). When a clone arises rapidly (50% per year on average), the classifier works better than the gold standard with a mean detection time 2.97±0.4 years (meant standard deviation) earlier than if the VAF was used (FIG. 7D). However, there is a relationship between how quickly a clone grows and how soon it will be detected with the gold standard VAF diagnosis and the FMC-CH classifier. When a clone grows slowly (≈6.25% per year) the difference in time to diagnosis using the classifier increases to 12.9±3.2 years (mean±standard deviation) after a VAF diagnosis. We see that the time between diagnosis in FIG. 7D increases faster for every halving of the expansion rate. Overall, this relationship can be quantified where the relative time to diagnosis from the VAF gold standard, $T_{\Delta}$, given the expansion rate is $T_{\Delta} \approx 25.05e^{-8.51E} - 3.7$ (FIG. 7E (right)).

Subclones within the simulations are all induced at 5 years. This early induction allows us to visualize the dynamics over the course of a 100-year simulation. While induction times of a driver mutation is possible this early in an individual's life, these drivers would likely expand very slowly, either through persistence (i.e., not lost during homogenization of HSCs during aging) or through slow continuous expansions, such as in our model. These clones will be detected at a point where this is of greater importance and may serve as an important delay for when closer monitoring is necessary for patients.

Retrospective Examination of Normal Whole Blood Cohorts

Figure 8A:
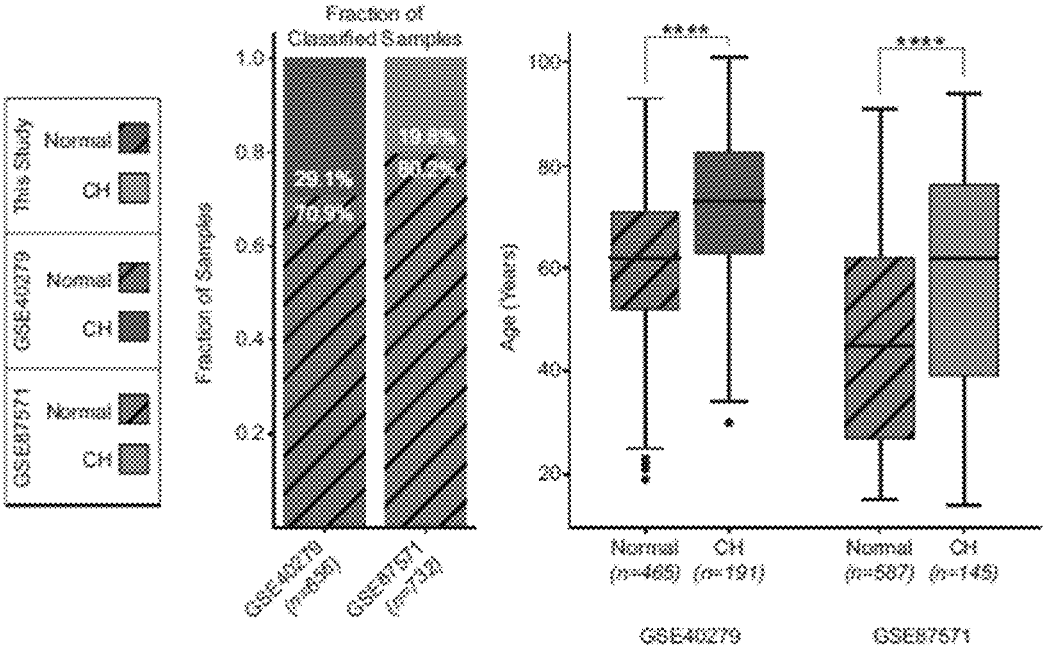
FIGS. 8A-8E illustrate retrospective analysis of 1,388 normal whole blood samples.
Figure 8B:
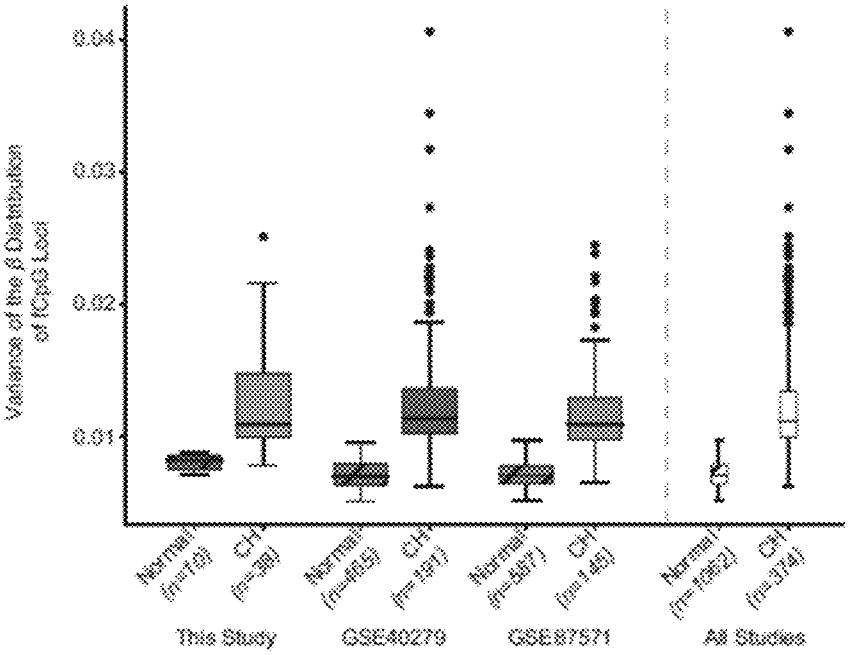
Figure 8C:
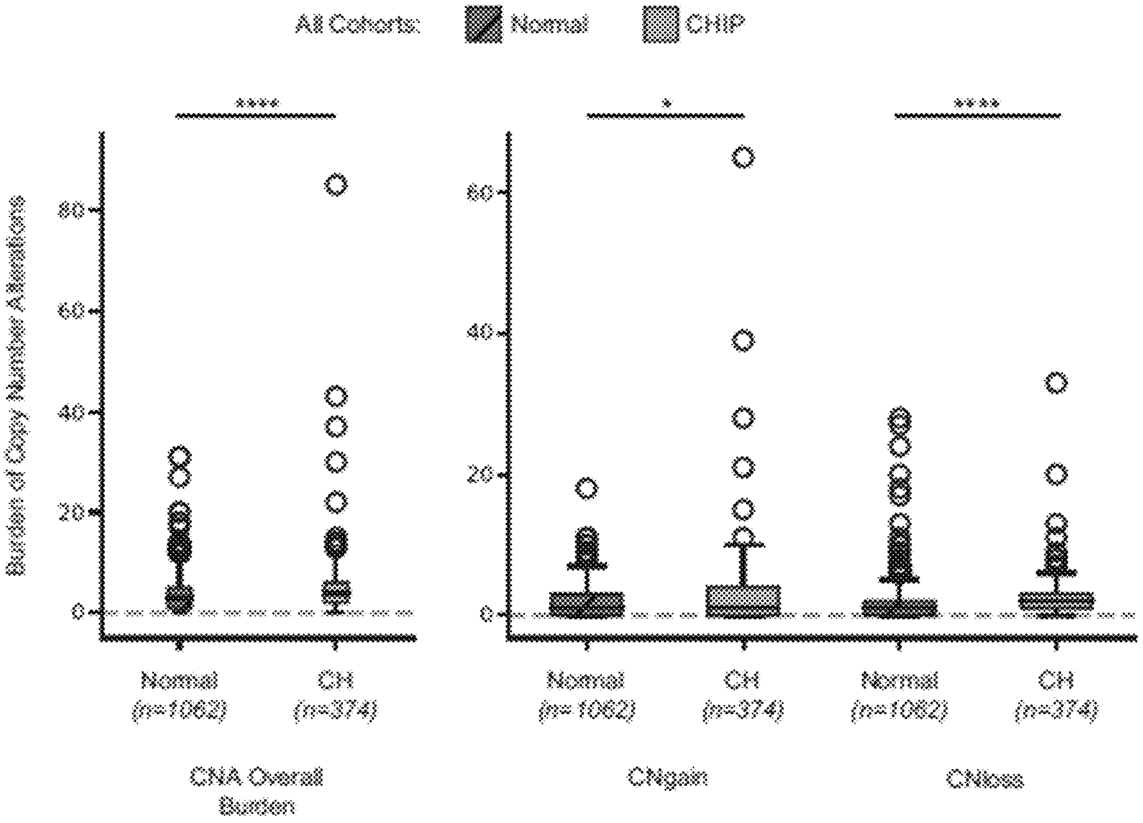

Based on the fCpG variances of the normal samples from the publicly available dataset we wanted to evaluate whether there was any evidence of CH present within these samples even if it may be below the clinical threshold of 2% VAF, given this has never been queried for these samples. For this we used the normal dataset of 656 patients used to derive fCpGs (GSE40279; FIG. 5A and FIG. 6C) and another large data set of normal patients with 732 patients (GSE87571). Using our CH classifier on each cohort we find support for classifying 29.1% (191 of 656) and 19.8% (145 of 732) as having CH within GSE40279 and GSE87571, respectively (FIG. 8A and FIG. 8B). Across both normal cohorts (n=1,388) our FMC-CH classifier finds 24.2% of individuals have CH.

Validation of Newly Diagnosed Clonal Hematopoiesis Patients

The current gold standard for validating the 24.2% of newly characterized patient samples would be to perform DNA sequencing on a panel of CH drivers to examine evidence of mutations with VAF≥2%. Neither of these cohorts have paired mutational data for validation purposes. However, we can examine whether expected characteristics of a CH cohort is present, and we can look for evidence of copy number alterations that could be significantly enriched within the newly identified CH patients.

Chances of Clonal Hematopoiesis Diagnosis Increases with Age

CH, as outlined above, is typically a disease largely limited to the elderly. By the age of 70, 10-15% of individuals will present with CH and by 85 years, more than 30% will have CH. As a sanity check we would expect that our FMC-CH classifier would classify CH in predominantly older patients. Across the two studies evaluated we see that the median age of normal samples is 54 years, significantly different from those with CH, whose median age is 70 years (−0.67 Cohen's d, $P=2.09*10^{-25}$ two-sided paired t-test). Individually for each cohort, we see that the median age for samples classified as CH from GSE40279 and GSE87571 is 73 and 62 years compared to the normal samples of 62 and 45 years, respectively (GSE40279, −0.77 Cohen's d, $P=3.13*10^{-18}$; GSE87571, −0.54 Cohen's d, $P=7.90*10^{-09}$). When comparing the age distributions for each of these two cohorts we see that GSE40279 is a significantly older cohort (64.0±13.7 years; mean±SD) compared to GSE87571, which also has a broader sampling of patient ages (47.4±20.9 years; mean±SD). This is reflected in the differences between the proportion of samples that are classified as CH between the two cohorts, where the older cohort, GSE40279, had 9.3% more CH classifications. For the entire cohort of patients (n=1,388) the median age is 58 years. Patients older than 58 years are more likely to be diagnosed with CH compared to those 58 or younger across these two cohorts (odds ratio (OR)=3.02, two-sided fisher exact test, $P=1.28*10^{-17}$).

Copy Number Alterations are Greater in Clonal Hematopoiesis Samples

Newly diagnosed CH samples from GSE40279 and GSE87571 exhibit fCpG variances consistent with the verified CH samples presented here (FIGS. 8A-8E). As illustrated through the analysis of publicly available malignancy methylation data with our samples (FIG. 5A and FIG. 6C) and alongside the HSC simulations (FIG. 5B and FIG. 7D) we expect that fCpG variances are driven higher by homogenization of the HSC pool, which we show correlates with age above. Within the newly classified CH samples no mutation data is present to be evaluated. Thus, we cannot confirm that the newly classified CH do or do not have CH driver SNVs. However, because CH is driven by copy number alterations as well there are several insights that can be gained by understanding the copy number burden differences between the classified normal versus CH samples. Due to these two normal cohorts not having DNA sequencing we are unable to rule out that either sample group has driver SNVs, but we hypothesize that several samples would exhibit a higher degree of aneuploidy.

We performed copy number calls using the methylation array data across the CH and normal cohorts to assess evidence of differences between the two groups of patients. We see that there are significant CNA burden differences overall, as well as for copy number losses and gains (FIG. 8C; two-sided Welch's t-test, $P=8.26*10^{-5}$, P=0.022, and P=0.00025, respectively). The average burden per patient across the CH cohorts is 4.7±6.1 CNAs (mean±standard deviation) while normal samples have significantly fewer CNAs at 3.7±3.3 (mean±standard deviation) in FIG. 8C. However, while the overall burden is significantly different the greatest difference driving that overall burden is the differences in the number of gains where the average copy number gains per patient is 2.6±4.8 (mean±standard deviation) for CH samples compared to 1.9±2.13 (mean±standard deviation) for the normal samples. While some retrospective, longitudinal studies diagnosed CH based simply on burden of SNVs (20), this is not the gold standard for diagnosis or validation of CH. Justification for this was the finding that this high burden of somatic alterations carried an 11.1 hazard ratio for the development of hematologic malignancy in CH patients. To evaluate differences in the CNA in the classified CH samples several analyses were conducted to evaluate additional evidence that those classifieds are indeed CH or normal samples.

Figure 8D:
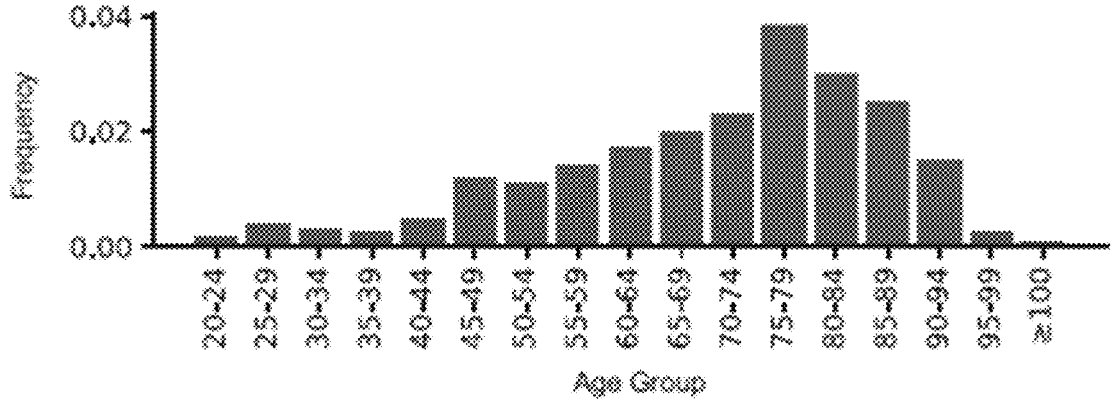

While burden alone may not support evidence of CH we posit that the distributions of CNA burdens is similar to those seen within clonal mosaicisms. In our data we lack information about subclonal proportions to perform the same analysis; however, given our understanding of what drives fCpG variance, loss of polyclonality in HSCs we can deduce that subclonal expansions within samples with higher fCpG variances are likely. Studies have shown that chromosomal abnormalities are present in expanded clones at frequencies of 7-95% representing clonal mosaicism, defined as CNA events with corresponding subclonalities above a threshold. The SNP array methodologies can resolve subclonal admixtures of normal to expanded subclones, something that is not possible using array-based methylation data. However, a previous study has analyzed the frequency of detectable clonal mosaic events by age in both cancer patients and cancer free patients. Similar to the age distributions seen for CH, whereby 10-15% of patients present with CH by the age of 70 and 30% by the age of 80, the frequency of individuals with detectable clonal mosaic events increases with age from 0.23% to 1.91% for those under 50 and between 75-79. The mosaic proportions within the study highlighted required mosaic proportions to be greater than 7%. Within our cohort of classified CH samples we see a similar reflection to the age distributions of the patients classified as being CH samples. The frequency of individuals with a presence of CNAs in the classified CH samples increase with age from 0.27% for those younger than 50 to 11.14% for those >70 years old (P=0.0013, chi-squared test; FIG. 8D). These results support that the samples classified as having CH based on fCpGs is likely.

Figure 8E:
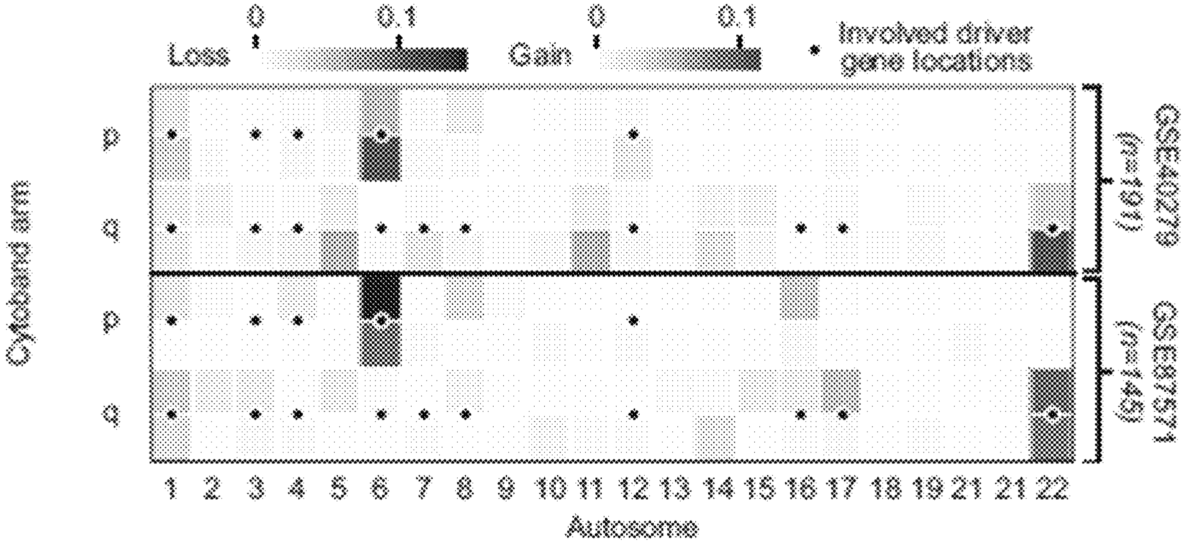

We next performed copy number calls using our classified normals as the controls to examine specific differences in genes and recurrent CNAs across different genomic regions that may be implicated in driving CH within the classified CH samples. Using our filtered, high confidence segmentation calls we annotated cytobands, determined genes within aneuploidy segments, and analyzed the genes to determine enrichment in a particular disease area or if overlap exists with known CH or cancer driver genes. On this set of CNAs we see enrichment in several disease classes associated with hematological diseases and malignancies. Of interest, we see significant gene enrichment for genes in regions exhibiting aneuploidy for disease classes related to acute and chronic lymphoblastic and myeloid leukemias as well as various other malignancies. In addition, we find 25 known oncogenic drivers associated with recurrent CNA regions exhibiting gains/losses in the CH cohorts (FIG. 8E). Together, with the CNA burden differences and age of individuals classified with CH we build confidence that the FMC-CH can accurately identify CH using fCpG sites.

Clonally Heterogeneous Landscapes in the Hematopoietic Stem Cell Pool

Our model of HSC dynamics, analysis of the CH cohort presented here, and analysis of publicly available data thus far has revealed that fCpG variances reflect underlying turnover and clonal expansions within the HSC pool using peripheral blood. FMCs in the peripheral blood can be used to diagnose CH; however, it is necessary to evaluate how the make-up of multiple predominant subclones could confound the diagnostic capabilities of the FMC-CH classifier and alter fCpG β distributions. To this end we can leverage our HSC model and explore the CH data.

Confounding Effects of Multiple Drivers in Silico

To assess the presence of multiple subclones we first must establish our baseline fCpG variance for a single clone and the corresponding detection times. From the in silico validation of the FMC-CH classifier, we showed that given a single clone, the expanding clone's expansion rate is the most important variable for the time that CH detection occurs. A rapidly expanding clone can be detected quickly, but an indolent expansion will take more time to be detected (FIG. 7D). However, in our data multiple subclonal drivers are present (FIG. 6A) motivating an analysis of the model where multiple clones can emerge at the same time or are acquired at different time points within simulations. We decided to examine the presence of 2 to 4 independent subclonal CH drivers (1 driver population serves as our baseline). We then spaced the induction of these concurrent founding populations out by 5, 10, and 15 years. For each of these concurrent drivers and their induction times we evaluated three different expansion rates that are all relatively slow (when compared to those that form a characteristic 'W' fCpG distribution). Expansions of symmetrically dividing populations were halted once a population reached 20% of the population (roughly corresponding to 10% VAF for purposes of comparisons (FIGS. 9A-D).

Figure 7E:
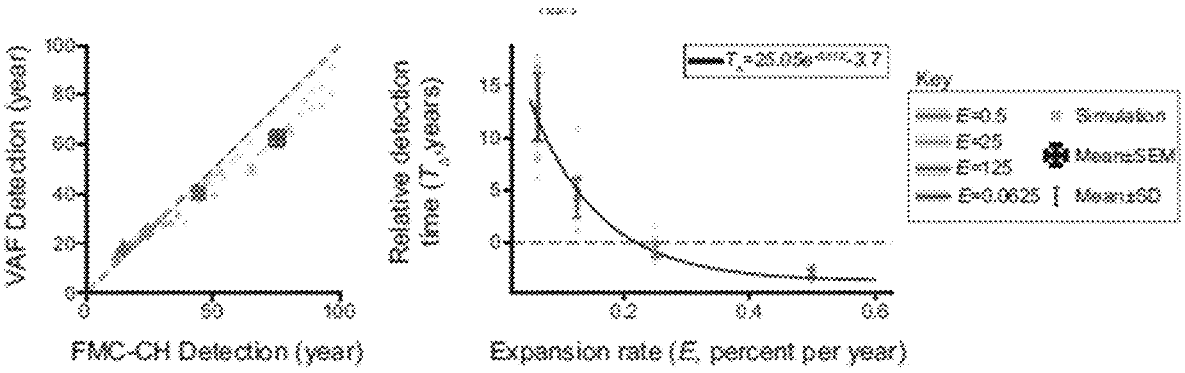
Figure 9B:
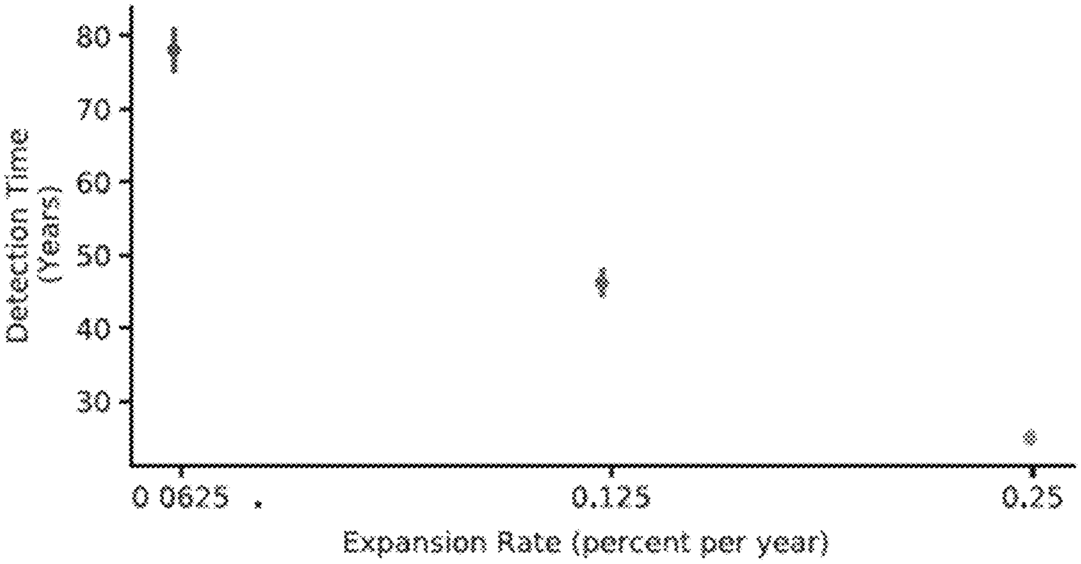
Figure 9C:
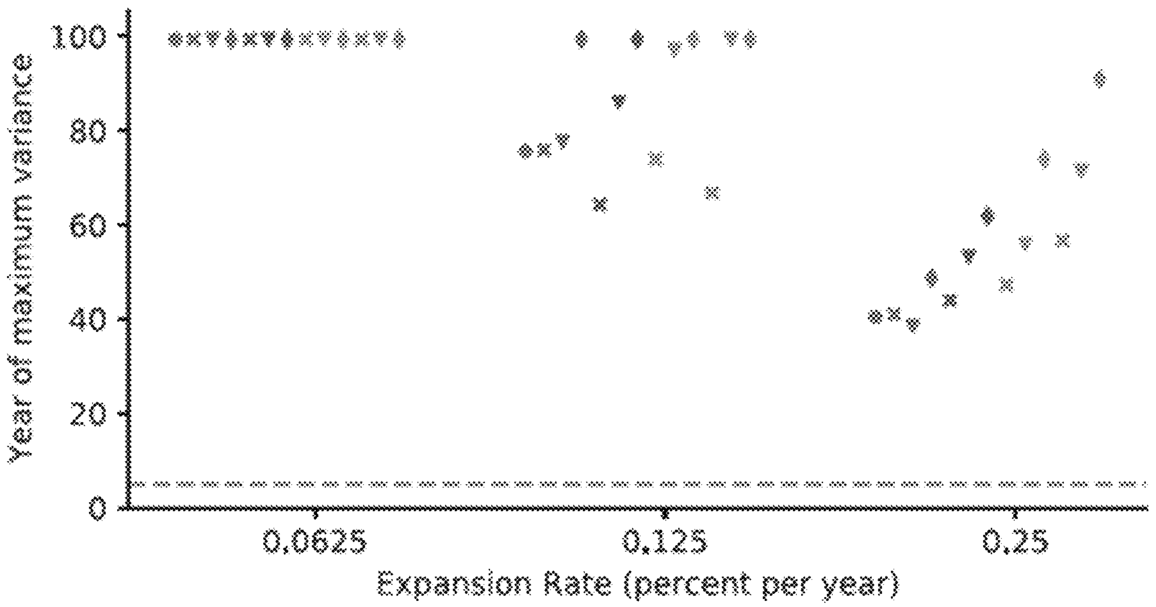

For our control, a single subclone with varied expansion rates, we see that the mean detection time across the three expansion rates is 20.0, 41.2, and 73.08 years after induction of the clone at year 5 for the three expansion rates considered (0.25, 0.125, 0.625, respectively; FIGS. 9A-B). This relationship is observed during the validation of the FMC-CH classifier as well, where the relative time to detection decreases exponentially as expansion rates increase (FIGS. 7D-E). When we com-pare the time to maximum fCpG variance when we introduce multiple concurrent subclones with different expansion rates and induction timings we see that the slowest clones rarely reach their maximum fCpG variances (and thus subclonal frequencies) in the 100-year simulation times irrespective of the induction spacing of multiple clones. Not until expansion rates are doubled, do we see the clones that are inducted at the same time reaching their maximum fCpG variances, when the induction times are spaced out, they fail to reach the maximum allowable frequency (10-15 years induction spacing of 3-4 subclones). For those third and fourth subclonal populations inducted with 15 year spacing it results in induction times at 35 and 50 years after the initial subclone, which at the slower expansion rates means it will not expand to an appreciable size prior to the end of the simulation (FIG. 9C).

Figure 9D:
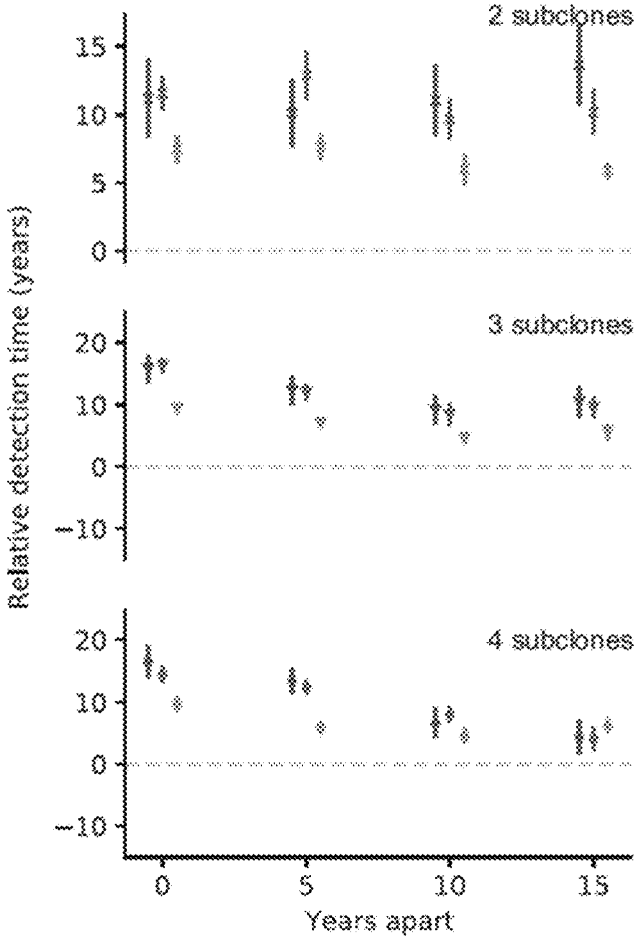

The detection time for CH in the presence of multiple subclones decreases the time to diagnosis (FIG. 9D). We would expect that the expansion of multiple, concur-rent subclones would increase the fCpG variance if expansions weren't proportional across all HSCs. When expansion rates are equal, and thus no functional heterogeneity and competition exists, the most important factor in driving detection time is the expansion rate, number of subclones, and how far apart their induction times are. The presence of two to four concurrent subclones, irrespective of their induction spacing, results in an earlier detection time by 5-15 years. For the largest number of concurrent clones, the expansion rates converge onto no relative difference in detection times at 15 years apart. This reflects that detection is driven by those first two clones that were inducted as later clones wouldn't have enough time to expand to an appreciable size to depart from the fCpG distribution seen in normal samples.

We know that the HSC compartment is highly heterogeneous, and we observe multiple subclones within our CH patients. Our model results suggest that there is an additive or multiplicative increase on fCpG variance as the number of subclones increases with various expansion rates. This prompts us to explore the presence of these multiple subclones and their relationship with FMC 6 distributions that we observe.

Multiple Subclonal Drivers in the Data

Figure 10A:
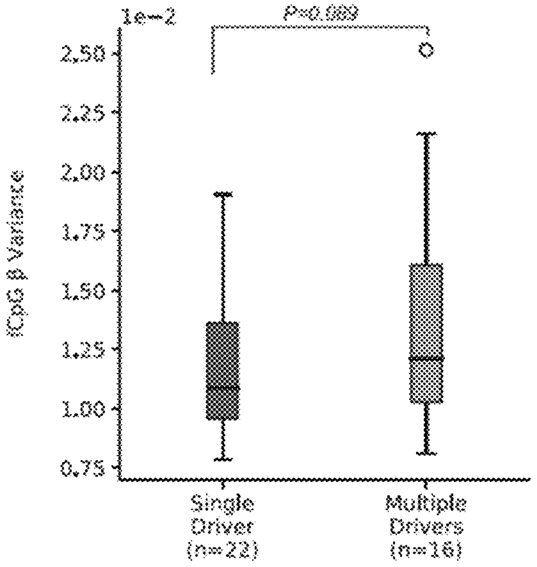
FIGS. 10A-10F illustrate concurrent driver mutations in the peripheral blood and bone marrow.

Within the CH samples presented, we observe a weak, positive correlation between the largest VAF driver (the gold standard in the clinic for CH diagnosis) with fCpG variance (FIG. 6B; r-squared=0.23, $P=2.3*10^{-3}$). Based on the results above from the HSC model, we expect that the sum of independent subclones could be an important consideration to re-evaluate the correlation of VAF with fCpG variance. We separated the CH cohort into samples that have multiple and single driver mutations, regardless of their frequency. When we examine the differences in fCpG variances we observe a nearly significant increase in variance for patients with more than one driver mutation ($0.013\pm4.0*10^{-3}$ mean±SD; n=16) compared to a single driver mutation (0.011±2.9*10 mean±SD; n=22) (Cohen's d=−0.58; two-sided Welch's t-test, P=0.089) (FIG. 10A).

Sequencing data is difficult to perform subclonal deconvolution on without deeper whole exome/genome sequencing, and even then, the resolution of low frequency subclones (such as those detected in CH with driver VAFs of 2-10%) is difficult to unravel. Several statistical frameworks attempt to perform this deconvolution, but cannot be applied here. Due to this, we can deduce two possibilities for this increased variance for samples with multiple driver mutations. The first being that the driver subclones arose independently and expand with an unknown slow expansion rate. This first possibility is far easier to assess within the data as we can simply sum the VAFs of all observed clones (ignoring the fact that other independent non-'driver' subclones are likely present). When we do this, we see that the cumulative frequency of the subclones for patients with more than one mutation have a significant shift in what the HSC model would consider to be the final blood frequency corresponding to higher fCpG variances (FIG. 10B (left)). The model results show that even at low expansion rates the presence of multiple subclones expanding leads to a larger fCpG variance. This means that multiple clones won't confound the classifiers' ability to detect CH. We re-evaluate the correlation between the cumulative frequency of the observed mutations and the fCpG variance and we observe a slightly stronger correlation than the single driver VAF (FIG. 10B (right); r-squared=0.28, $P=5.8*10^{-4}$). The second possibility is that the smaller frequency drivers are acquired mutations in daughter cells of the first clone resulting in a modulated expansion rate conveyed by this second driver. Importantly, this modulation of the expansion rate, as seen in the in silico HSC simulations wouldn't lead to a decrease in the fCpG variance.

Paired Bone Marrow from Patients with Clonal Hematopoiesis

The PB is not the site of HSC, rather, HSCs are primarily located in the axial skeleton BM where hematopoiesis begins with cells eventually committing to their identities (one of several cell types, lymphoid or myeloid terminally differentiated cell) and move out to the peripheral blood. Most measurements within the PB are reflections of events that occur within the BM, but few studies confirm this. Importantly for fCpG distributions, we are interested to know if we can accurately capture the underlying distribution of the HSCs from the terminally differentiated PB. For the fCpG β distribution to accurately reflect that which is seen in the BM individual subclones would have to be giving rise to equal proportions of various blood cell types. This is still a widely open area of interest, but one study found that the production of blood is highly polyclonal, deriving from a large number of HSC. In our study we have paired methylation data derived from PB with which corresponding DNA sequences evaluate the presence of CH subclones. Here we also present the paired BM DNA sequencing results to examine whether PB or BM subclones are of equal sizes and whether their subclonal frequencies correlate with fCpG variance (FIGS. 10C-F).

The presence of paired BM provides several sanity checks for both the interpretation of the PB findings as well as the fCpG variances. We see that all variant allele frequencies are similar between the BM and PB (FIG. 10C). We see that as the frequency of the CH driver mutations increase in the BM (presumably the oldest subclones) they are slightly higher in the PB, but a strong correlation exists (r-squared=0.86; $P=3.5*10^{-30}$). We evaluated whether DNMT3A or TET2 mutations saw a departure from this correlation and no significant difference was observed across mutation types (r-squared=0.91 and 0.77 with P-values<<0.0001, respectively). Beyond this correlation, pairwise comparisons across patients reveal there is no significant differences between the variant allele frequencies of the driver subclones between PB and BM (Wilcoxon signed-rank test; P=0.36). For some of the dominant driver mutations (used for diagnosis) we see slight differences in their VAFs, but these differences are often within an expected margin of technical error from DNA sequencing (FIG. 10D).

Figure 10B:
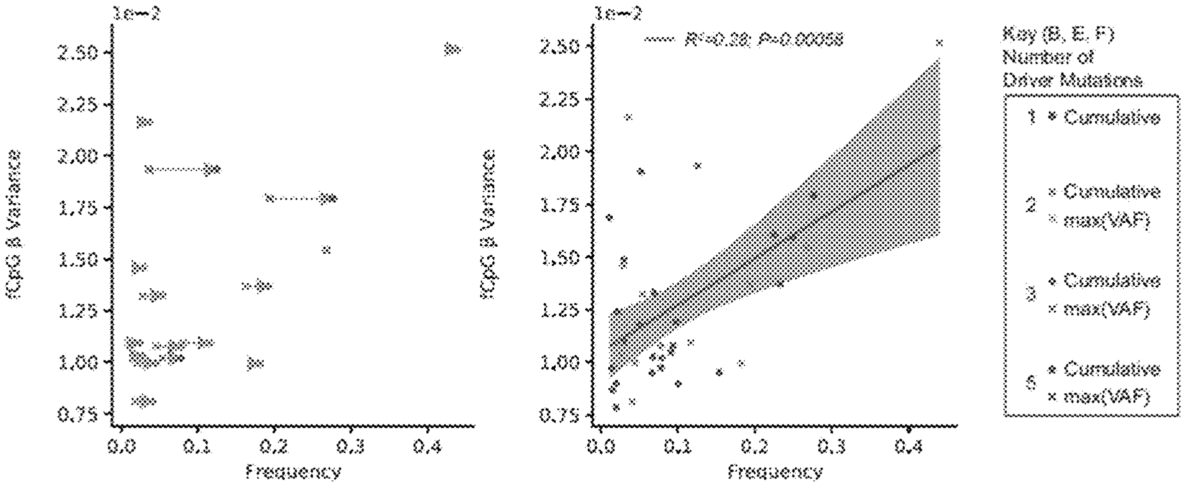
Figure 10C:
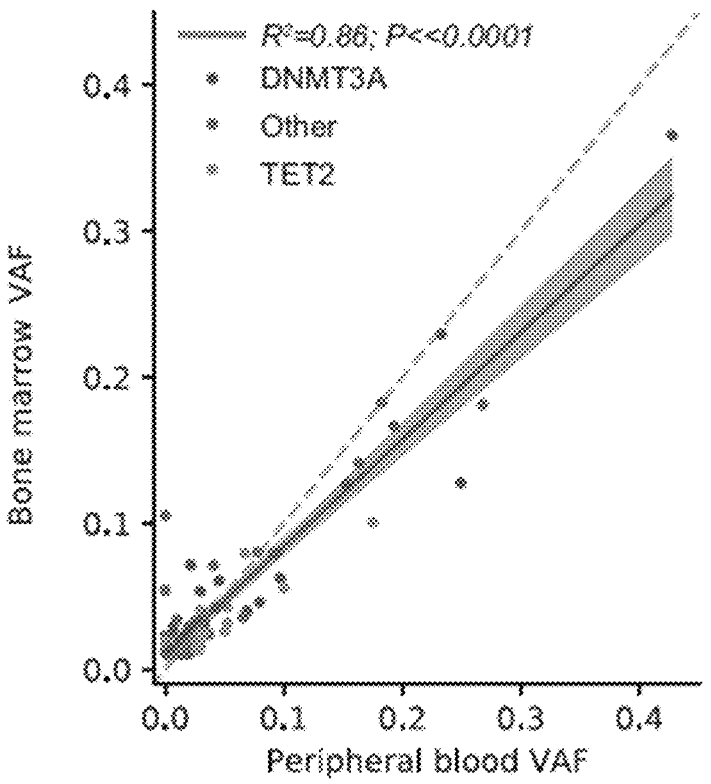
Figure 10D:
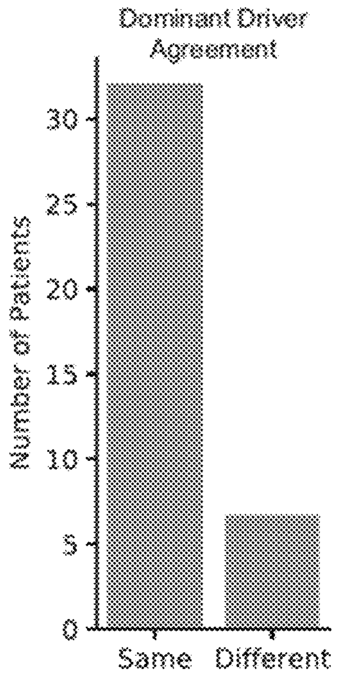
Figure 10E:
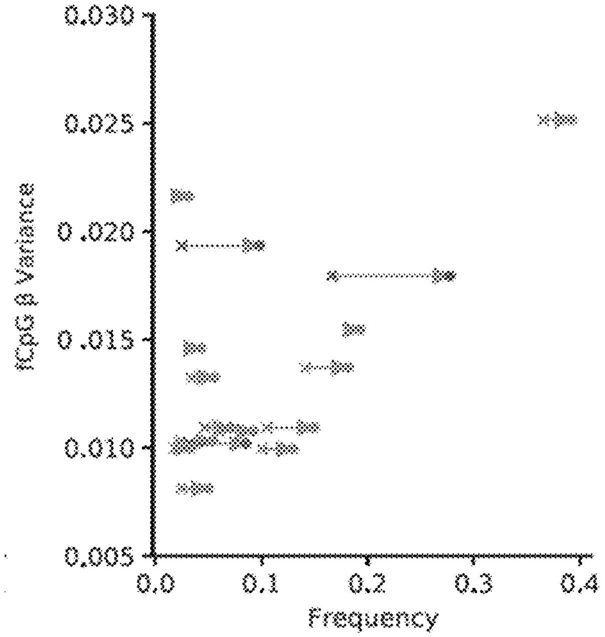
Figure 10F:
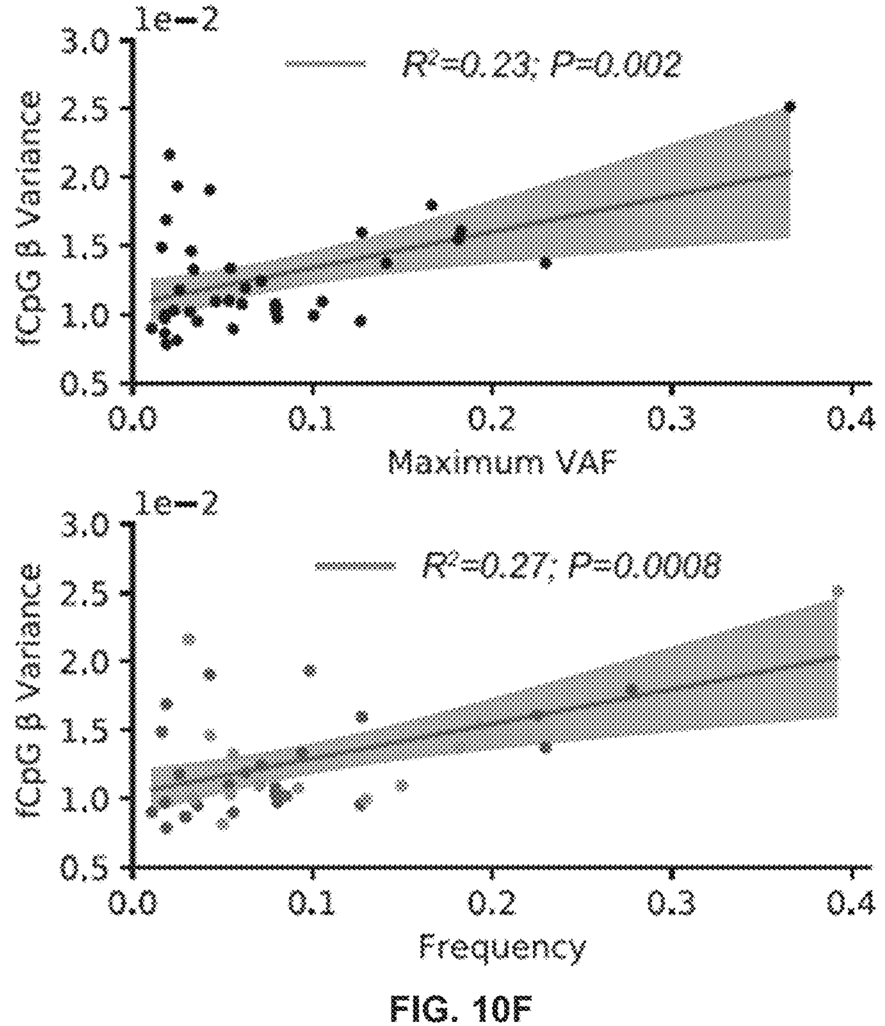

We next wanted to evaluate how well the fCpG β distribution correlates with the VAF of the putative drivers from the BM to see if similar correlations are found as those seen in the PB (FIG. 10B). When we perform the same correction as applied to the samples with multiple subclonal drivers to evaluate the correlations we see the same increased correlation when taking the cumulative sum of putative driver VAF (FIG. 10F).

Single Cell Sequencing of Clonal Hematopoiesis Patients Confirms Subclonal Structures Our understanding of CH, aging of HSCs populations, and accumulation of mutations within normal tissues resulting in mosaic tissue suggests that we are likely to observe a vast collection of distinct populations of HSC subclones. Some of these subclonal populations ought to have acquired the necessary drivers for CH with their likelihood increasing as an individual ages. This prompted our analysis of concurrent driver clones as it relates to our ability to detect CH with our FMC-CH classifier (FIGS. 9A-D) and the cumulative frequency correlation with fCpG variance in the data (FIGS. 10A-E). However, based on our understanding of multi-stage tumorigenesis it is highly likely that some of the observed driver mutations present in our CH samples with multiple drivers are nested and acquired at some point within the parent driver's lineage. With high resolution whole exome/genome sequencing we could potentially deconvolve the subclonal structure of these mutations, but these are low frequency mutations that would be difficult to disentangle from one another. In-stead, single cell sequencing offers the best resolution currently to reliably uncover the subclonal structures of these mutations to determine if a frequency adjustment is necessary to examine correlate with fCpG variance.

Figure 11A:
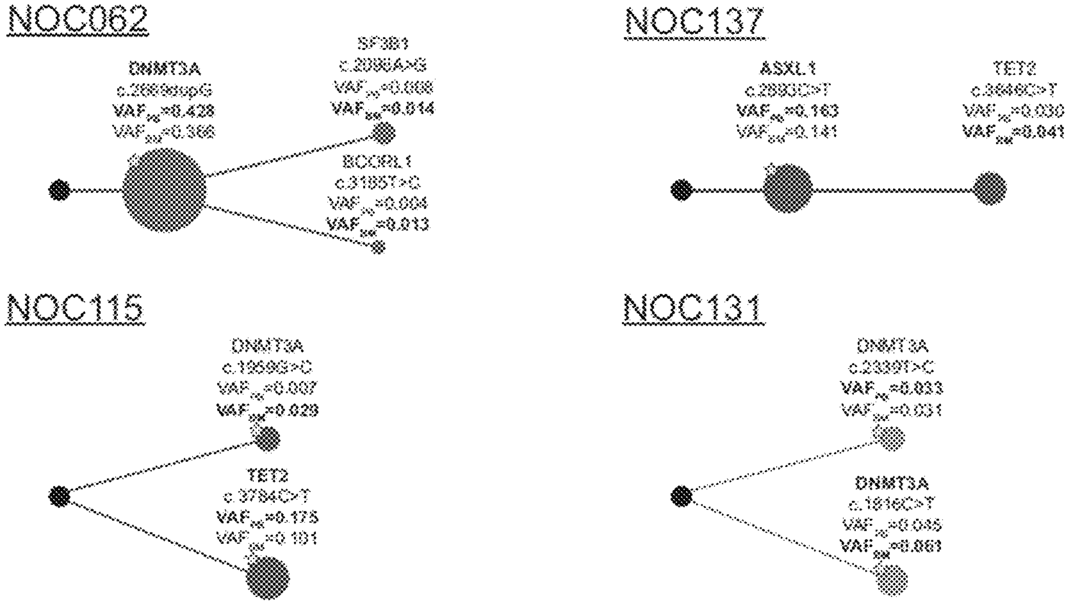
FIGS. 11A-11E illustrates single cell sequencing confirms subclonal composition. Single cell sequencing conducted on four samples to confirm subclonal composition and nested structure of mutations.
Figure 11B:
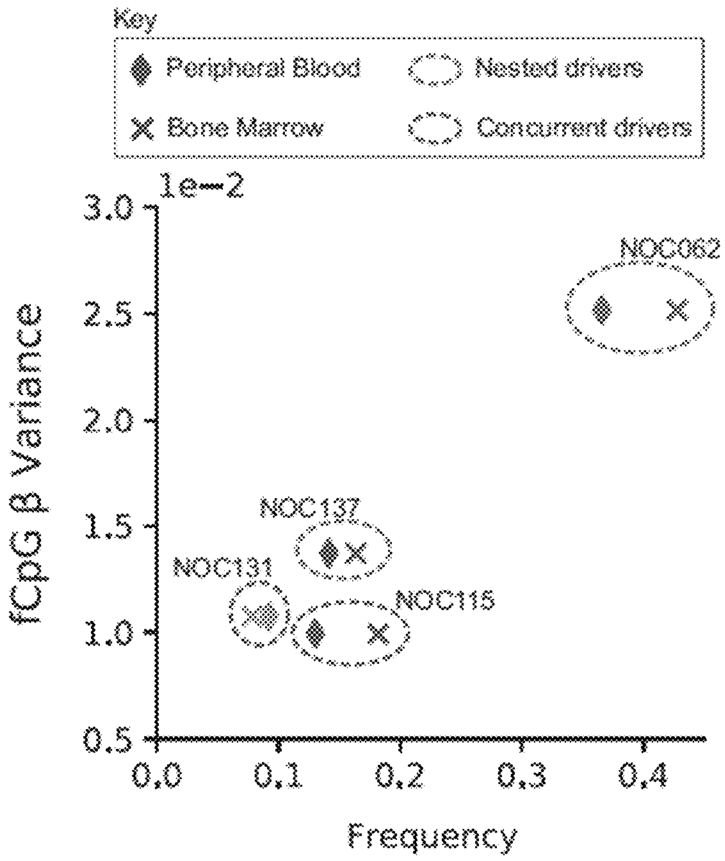

We performed single cell sequencing on four of our CH samples who had drivers with VAFs>5% and showed presence of a DNMT3A or TET2 mutation (NOC062, NOC137, NOC115, and NOC131). Fortuitously, two of these samples exhibited sub-clonal structures that were nested (NOC062 and NOC137), while the other two were concurrent CH subclones (NOC115 and NOC131) (FIG. 11A). Interestingly, we see a relationship within these four samples where there appears to be an unknown threshold where the frequency of a subclone is larger in the bone marrow while the mutation is small enough, while it is larger in the PB if it is a larger clone. There are too few samples to draw any definitive conclusions here. However, this could indicate that the clones that have been around longer have given rise to cells with longer half-lives that persist longer in the PB rather than cells with rapid turnover. This could occur for an indolently expanding clone that arose early and has a low population frequency and thus a low fCpG variance or for a clone with a moderate expansion rate that arose in some time in the not as distant past; however, in turn this would result in a higher fCpG variance which occurs for larger cumulative sub-clones or faster expanding clones (in the model this is shown in FIG. 5A and FIGS. 9A-D; for the data we illustrate this with our correlations in FIGS. 10A-F). PB cell half-lives once they have fully differentiated, exiting the BM, are all relatively short with lineage tracing studies revealing half-lives between 12 hours for monocytes and 4-7 weeks for B cells.

Modeling Nested Subclonal Expansions

Figure 11C:
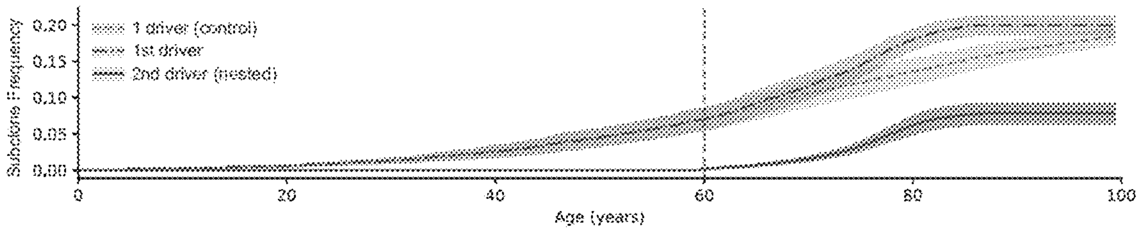

So far, we have presented model simulations with distinct subclonal populations with varied expansion rates, various years between mutation induction, and numbers of sub-clones. However, given that nested structures exist within the data it's necessary to also simulate the occurrence of multiple subclones with one originating as the daughter from the initial driver population as confirmed in two of our samples. Here we initialize the first clone at five years with the slowest expansion rate of 6.25 percent per year. Unlike the previous simulations we introduce a new founder clone as a daughter of the initial subclone at 60 years (the timing of this second subclone was chosen arbitrarily, but it needed to occur early enough to be seen by the 100-year stopping point of the simulations). There are numerous approaches to determining fitness gains conveyed by the acquisition of passenger mutations and additional drivers acquired within a subclonal population, but here we assume that a modest fitness increase is conveyed as a faster expansion rate for that subclonal population. Where its expansion rate increases 200% (2×) to 12.5 percent per year (the moderate expansions seen in previous simulations). We permit these subclones to expand until the driver reaches a final population frequency of 20% (FIG. 11C).

Figure 11D:
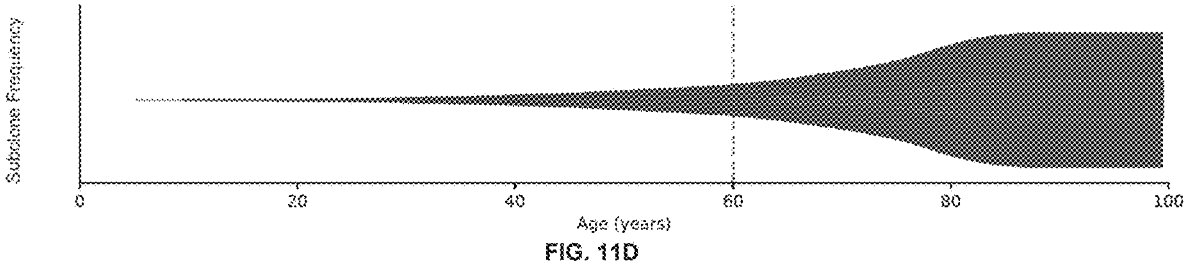
Figure 11E:
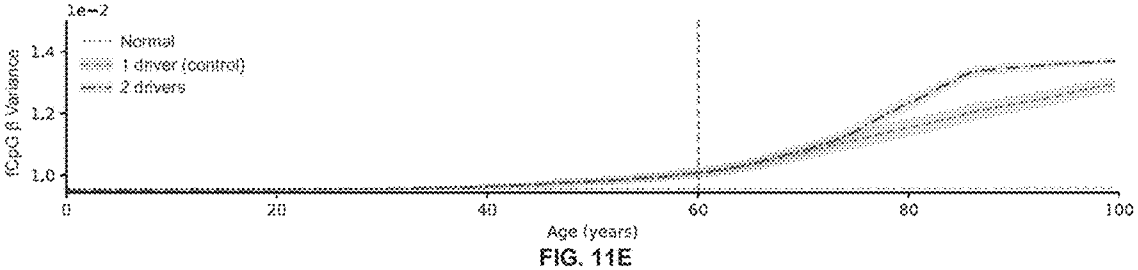

We see that the nested subclonal causes an increase in the fCpG variance over the control where a single subclone grows at a steady 6.25 percent per year (FIG. 11E). We see that the frequency of the initial population diverges ten years after the introduction of the 2nd driver with an appreciable growth of the 2nd clone between induction and reaching its final frequency. Qualitatively, these frequencies are approximately similar to those observed for patient NOC137 whose frequency of the primary driver VAF is 0.16 for ASXL1 and its nested driver VAF, TET2, is 0.041 with a corresponding fCpG variance just under 1.5 (FIGS. 11C-E). This suggests that having a known frequency and corresponding fCpG β distribution could be valuable in providing insights into expansion times and clone inductions.

Discussion

Through the work presented in this example we have orthogonally validated FMCs to show that not only are fCpGs found in the crypts of the colon, small intestine, and endometrium, but they exist in HSCs as well. Large numbers of fCpG sites reversibly switch their methylation status like an erratically swinging pendulum between 0%, 50% and 100% (representing homozygous and heterozygous (de) methylation). In the polyclonal populations, exemplified by HSC, fluctuations are unsynchronized between individual cells and fCpG methylation is saturated at 50%. This is distinct from clonal populations that form the characteristic W-shaped distribution with modal peaks at 0%, 50% and 100% methylation.

Within the scope of hematopoietic cells we show that fCpG dynamics are present and useful to reconstruct clonal dynamics. The identity of the fCpG sites in hematopoietic cells differs from those in the epithelium, likely reflecting that fCpGs tend to be found within non-expressed genes and the fact that gene expression patterns vary between tissues. We illustrate the ability of fCpG sites to be used to detect CH through our HSC model of symmetrically expanding sub-clonal populations corresponding to an increase in average fCpG variances with clonality and characteristic W-shaped distributions present in acute leukemias (FIGS. 5A-B). Chronic leukemias had intermediate fCpG variance increases and generally lacked W-shaped distributions, likely reflecting their slower growth.

Development of HSC pools ends how they begin, more homogeneous in children and elderly. HSCs begin relatively homogenous during embryogenesis and expanding for the first two decades (<20 years) giving rise to a highly heterogeneous mixture of HSCs before losing some HSCs through aging. In acute leukemia cohorts of older patients versus pediatric patients we see that pediatric patients exhibit higher fCpG variance likely reflecting the differences in initial HSC dynamics. On the other end of the life span, where HSCs diminish in numbers and exhibit an age related incidence of CH we see fCpG variances increased.

Due to the age-related incidence of CH it is important to consider how important CH may be in the development of malignancies. Given that across most tissues in the human body somatic alterations are ubiquitous, and may not pose much risk to further developing of malignancies, it is paramount to be able to tease apart what underlying dynamics are clinically relevant to future malignancies and which are simply a part of human aging. To this end we show that we can leverage FMCs to determine the extent of CH. The approach developed here adds significant value in that it is more sensitive to the underlying dynamics than the current gold standard based on variant frequencies. FMC have the added value of being agnostic to the underlying genomic alterations for purposes of diagnosing CH; further, they are more sensitive to faster expanding clones or the presence of multiple subclones with malignant potential.

Example 2

Diagnosis of Clonal Hematopoiesis

Described below is a molecular diagnostic method that leverages patient derived data to construct an ensemble machine learning algorithm to provide a patient diagnosis of clonal hematopoiesis (CH) and pre-cancerous hematological conditions encompassing age-related clonal hematopoiesis (ARCH) and clonal hematopoiesis of indeterminate potential (CHIP) using specific DNA methylation fluctuating CpG (fCpG) sites that serve as a fluctuating methylation clock (FMC).

Prognosis of CH to Hematological Malignancies

Combining FMCs, a patient specific in silico hematopoietic stem cell (HSC) model, and patient DNA alteration markers (collectively single nucleotide variants (SNVs), copy number alterations (CNAs), and structural variants (SVs)) with associated patient outcomes, a patient prognosis can be constructed to assign risk of progression to a hematological malignancy.

Longitudinal Monitoring and Early Prediction of CH

Through longitudinal collection of fCpG measurements and subsequent use of this molecular diagnostic process as described above, an algorithmic interface can be used to construct a patient specific trajectory to predict when and if a patient will present with clinically actionable CH to construct a monitoring schedule for patient follow-ups, clinical intervention, and clinical decision making.

Consumer Health Choices and CH Progression Risk

A patient and clinician user interface can provide patients with information on risks of lifestyle choices given their age, extent of clonal homogeneity, and possible outcomes calculated as probabilities using patient associated outcomes and in silico models. Such outcomes can include, but is not limited to, a lifetime risk of: hematological malignancy development, major cardiovascular events such stroke and heart attack, and/or development of epithelial neoplasia.

Diagnosis of Hematological Malignancy

Using the molecular diagnostic method described above and refined criteria of observed fCpG measurements, a molecular diagnosis of a hematological malignancy can be provided for clinical follow-up and therapeutic intervention.

Treatment Recommendations

Using fCpG monitoring of patients with hematological malignancy combined with DNA alteration markers provides risk and patient stratification based on assessing aggressiveness of disease.

Risks of Unsuccessful Therapeutic Intervention

Using FMC DNA methylation measurements can be used to provide risk assessments for treatment associated hematological malignancies (e.g., treatment associated myeloid neoplasia (tMN)) while patients undergo therapeutic interventions for non-hematological malignancies. The same collected data and measurements provides risk assessments for autologous stem-cell transplantation success.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method comprising:
- receiving patient data associated with a blood specimen from a subject, the patient data comprising fluctuating methylation clock (FMC) data including DNA methylation fluctuation data for a plurality of fluctuating CpG (fCpG) sites;
- generating a hematopoiesis model that describes a clonal expansion of a plurality of cells from the blood specimen using the DNA methylation fluctuation data as clocks in the cells to model repeated cycling between methylated and unmethylated states;
- determining, based on a plurality of parameters for normal hematopoiesis, an fCpG variance measure and an fCpG distribution measure for the hematopoiesis model;
- inputting at least a portion of the FMC data into a trained machine learning model, wherein the trained machine learning model is trained using sub-sampled fCpG site data; and
- predicting, using the trained machine learning model and based at least in part on the determined fCpG variance measure and fCpG distribution measure, a hematological condition in the subject.

2. The computer-implemented method of claim 1, wherein the patient data further comprises one or more DNA alteration markers.

3. The computer-implemented method of claim 2, wherein the one or more DNA alteration markers comprise a single nucleotide variant (SNV), a copy number alteration (CNA), or a structural variant (SV).

4. The computer-implemented method of claim 1, wherein the step of predicting, using the trained machine learning model, the hematological condition comprises diagnosing the subject with the hematological condition.

5. The computer-implemented method of claim 1, wherein the step of predicting, using the trained machine learning model, the hematological condition comprises providing a prognosis of the hematological condition.

6. The computer-implemented method of claim 1, wherein the hematological condition is clonal hematopoiesis (CH).

7. The computer-implemented method of claim 1, wherein the hematological condition is clonal hematopoiesis of indeterminate potential (CHIP).

8. The computer-implemented method of claim 1, wherein the hematological condition is age related clonal hematopoiesis (ARCH).

9. The computer-implemented method of claim 1, wherein the trained machine learning model is a random forest classifier.

10. The computer-implemented method of claim 1, wherein the plurality of parameters for normal hematopoiesis includes at least one of numbers of hematopoietic stem cells (HSCs), a number of possible division events, methylation and/or demethylation rates for the fCpG sites, HSC replacement dynamics, a cell expansion rate, and a final blood frequency of clonal expansion.

11. A method comprising:
- receiving a blood specimen from a subject;
- obtaining, using a microarray, fluctuating methylation clock (FMC) data associated with the blood specimen, wherein the FMC data includes DNA methylation fluctuation data for a plurality of fluctuating CpG (fCpG) sites;
- generating a hematopoiesis model that describes a clonal expansion of a plurality of cells from the blood specimen using the DNA methylation fluctuation data as clocks in the cells to model repeated cycling between methylated and unmethylated states;
- determining, based on a plurality of parameters for normal hematopoiesis, an fCpG variance measure and an fCpG distribution measure for the hematopoiesis model;
- inputting, using a computing device, at least a portion of the FMC data into a trained machine learning model, wherein the trained machine learning model is trained using sub-sampled fCpG site data; and
- predicting, using the trained machine learning model and based at least in part on the determined fCpG variance measure and fCpG distribution measure, a hematological condition in the subject.

12. The method of claim 11, further comprising recommending, using the computing device, a course of treatment for the subject based on the predicted hematological condition.

13. The method of claim 12, further comprising performing the course of treatment on the subject based on the predicted hematological condition.

14. A system comprising:
- at least one processor and a memory operably coupled to the at least one processor, the memory having computer-executable instructions stored thereon that, when executed by the at least one processor, cause the processor to:
- receive patient data associated with a blood specimen from a subject, the patient data comprising fluctuating methylation clock (FMC) data, wherein the FMC data includes DNA methylation fluctuation data for a plurality of fluctuating CpG (fCpG) sites;
- generate a hematopoiesis model that describes a clonal expansion of a plurality of cells from the blood specimen using the DNA methylation fluctuation data as clocks in the cells to model repeated cycling between methylated and unmethylated states;

determine, based on a plurality of parameters for normal hematopoiesis, an fCpG variance measure and an fCpG distribution measure for the hematopoiesis model;

input at least a portion of the FMC data into a trained machine learning model, wherein the trained machine learning model is trained using sub-sampled fCpG site data; and receive, from the trained machine learning model and based at least in part on the determined fCpG variance measure and fCpG distribution measure, a predicted hematological condition in the subject.

15. The system of claim 1, wherein the patient data further comprises one or more DNA alteration markers.

16. The system of claim 15, wherein the one or more DNA alteration markers comprise a single nucleotide variant (SNV), a copy number alteration (CNA), or a structural variant (SV).

17. The system of claim 14, wherein the step of receiving, using the trained machine learning model, the predicted hematological condition comprises receiving a diagnosis or prognosis of the hematological condition.

18. The system of claim 14, wherein the predicted hematological condition is clonal hematopoiesis (CH), clonal hematopoiesis of indeterminate potential (CHIP), or age related clonal hematopoiesis (ARCH).

19. The system of claim 14, wherein the trained machine learning model is a random forest classifier.

* * * * *